United States Patent
Yamada et al.

(10) Patent No.: US 9,943,709 B2
(45) Date of Patent: *Apr. 17, 2018

(54) SKIN CLEANSING COMPOSITION

(71) Applicant: KAO CORPORATION, Chuo-ku (JP)

(72) Inventors: Kouhei Yamada, Sumida-ku (JP);
Atsushi Tomokuni, Shinagawa-ku (JP);
Koji Tanaka, Shinagawa-ku (JP);
Daisuke Sawa, Sumida-ku (JP);
Takashi Kawai, Koto-ku (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/787,585

(22) PCT Filed: Apr. 28, 2014

(86) PCT No.: PCT/JP2014/061856
§ 371 (c)(1),
(2) Date: Oct. 28, 2015

(87) PCT Pub. No.: WO2014/178371
PCT Pub. Date: Nov. 6, 2014

(65) Prior Publication Data
US 2016/0101036 A1    Apr. 14, 2016

(30) Foreign Application Priority Data

Apr. 30, 2013  (JP) ................................. 2013-096092
Apr. 30, 2013  (JP) ................................. 2013-096093
May 31, 2013  (JP) ................................. 2013-116492

(51) Int. Cl.
*C11D 3/18*  (2006.01)
*C11D 3/20*  (2006.01)
(Continued)

(52) U.S. Cl.
CPC .............. *A61Q 1/14* (2013.01); *A61K 8/0208* (2013.01); *A61K 8/31* (2013.01); *A61K 8/33* (2013.01); *A61K 8/8152* (2013.01); *A61Q 19/10* (2013.01)

(58) Field of Classification Search
CPC ........... C11D 3/18; C11D 3/20; C11D 3/3757; A61K 8/31; A61K 8/33; A61K 8/36;
(Continued)

(56) References Cited

U.S. PATENT DOCUMENTS 5,585,104 A   12/1996  Ha et al.
7,094,462 B1   8/2006  Yokoyama et al.
(Continued)

FOREIGN PATENT DOCUMENTS

CN   1511511 A   7/2004
CN   1718427 A   1/2006
(Continued)

OTHER PUBLICATIONS

International Search Report dated Jul. 22, 2014 in PCT/JP2014/061856 filed Apr. 28, 2014.

*Primary Examiner* — Brian P Mruk
(74) *Attorney, Agent, or Firm* — Oblon, McClelland, Maier & Neustadt, L.L.P.

(57) ABSTRACT

Provided is a skin cleansing composition comprising the following components (A), (B), (C), (D), and (E): (A) 0.1 to 25 mass % of an ether oil which is in a liquid state at 25° C., (B) 0.003 to 1 mass % of a water-soluble polymer comprising acrylic acid or methacrylic acid as a constitutional unit, (C) 1 to 30 mass % of a hydrocarbon oil having a viscosity of 15 mPa·s or lower at 30° C., (D) 60 to 95 mass % of water, and (E) 0.49 mass % or less of a nonionic surfactant having an HLB of larger than 9, wherein the mass ratio of the component (B) to the component (A), (B)/(A) is from
(Continued)

0.0001 to 0.1, and the mass ratio between the component (A) and the component (C), (A)/((A)+(C)) is from 0.05 to 0.9.

18 Claims, 1 Drawing Sheet

(51) Int. Cl.
  *A61K 8/31* (2006.01)
  *A61K 8/33* (2006.01)
  *A61K 8/36* (2006.01)
  *A61K 8/81* (2006.01)
  *A61K 8/92* (2006.01)
  *A61Q 1/14* (2006.01)
  *A61Q 19/00* (2006.01)
  *A61Q 19/10* (2006.01)
  *A61K 8/02* (2006.01)

(58) Field of Classification Search
  CPC ... A61K 8/81; A61K 8/92; A61Q 1/14; A61Q 19/00
  See application file for complete search history.

(56) References Cited

U.S. PATENT DOCUMENTS

| | | |
|---|---|---|
| 2001/0046948 A1 | 11/2001 | Kaneda et al. |
| 2002/0098763 A1 | 7/2002 | Yoshikawa et al. |
| 2005/0186167 A1 | 8/2005 | Ueda et al. |
| 2006/0039956 A1 | 2/2006 | Hensen et al. |
| 2012/0263671 A1* | 10/2012 | Okubo ................. A61K 8/0295 424/78.02 |
| 2012/0294912 A1* | 11/2012 | Fukui ................... A61K 8/0254 424/401 |
| 2014/0142016 A1 | 5/2014 | Tomokuni et al. |
| 2016/0101036 A1 | 4/2016 | Yamada et al. |

FOREIGN PATENT DOCUMENTS

| | | | |
|---|---|---|---|
| JP | 11-503461 A | 3/1999 | |
| JP | 2000-191438 A | 7/2000 | |
| JP | 2000-290899 A | 10/2000 | |
| JP | 2001-302450 A | 10/2001 | |
| JP | 2002-68936 A | 3/2002 | |
| JP | 2002-209823 A | 7/2002 | |
| JP | 2002-542274 A | 12/2002 | |
| JP | 2003-93152 A | 4/2003 | |
| JP | 2003-164407 A | 6/2003 | |
| JP | 2004-339212 A | 12/2004 | |
| JP | 2005-511554 A | 4/2005 | |
| JP | 2005-145872 A | 6/2005 | |
| JP | 2005-239561 A | 9/2005 | |
| JP | 2006-022412 * | 1/2006 | ............... D04H 1/42 |
| JP | 2006-22412 A | 1/2006 | |
| JP | 2006-110796 A | 4/2006 | |
| JP | 2006-223454 A | 8/2006 | |
| JP | 2007-68986 A | 3/2007 | |
| JP | 2008-22412 A | 1/2008 | |
| JP | 2008-150317 A | 7/2008 | |
| JP | 2008-202153 A | 9/2008 | |
| JP | 2009-242340 A | 10/2009 | |
| JP | 2010/280597 A | 12/2010 | |
| JP | 2012-201622 A | 10/2012 | |
| JP | 2013-32348 A | 2/2013 | |
| JP | 2014-218436 A | 11/2014 | |
| JP | 2014-231506 A | 12/2014 | |
| JP | 5705912 B2 | 4/2015 | |
| WO | 2000/64408 | 11/2000 | |
| WO | 2013/005422 A1 | 1/2013 | |

* cited by examiner

SKIN CLEANSING COMPOSITION

TECHNICAL FIELD

The present invention relates to a skin cleansing composition and a skin cleansing sheet.

BACKGROUND ART

Various cleansing agents for removing traces of makeup have been developed according to the diversification of makeup products or the preference of consumers. In recent years, the number of stay-put waterproof mascara has increased. Thus, cleansing agents which can thoroughly remove even stay-put waterproof mascara have been studied, and combinations of various oil agents, nonionic surfactants, and the like have been studied (e.g., Patent Literatures 1 to 3).

Also, cleansing sheets have heretofore been known in which a base material sheet such as a nonwoven is impregnated with a cleansing agent. For example, a sheet for cleaning, wherein the basis weight of the nonwoven serving as a base material sheet, the type of its fibers, and components contained in the cleansing agent are specified (Patent Literatures 4 and 5), a wet wipe product which enhances skin barrier (Patent Literature 6), and a cleansing material, wherein the viscosity of the cleansing agent is specified (Patent Literature 7) have been studied.

(Patent Literature 1) JP-A-2000-191438
(Patent Literature 2) JP-A-2004-339212
(Patent Literature 3) JP-A-2009-242340
(Patent Literature 4) JP-A-2003-164407
(Patent Literature 5) JP-A-2002-209823
(Patent Literature 6) JP-A-2002-542274
(Patent Literature 7) JP-A-2001-302450

SUMMARY OF THE INVENTION

The present invention relates to a skin cleansing composition comprising the following components (A), (B), (C), (D), and (E):
(A) 0.1 to 25 mass % of an ether oil which is in a liquid state at 25° C.,
(B) 0.003 to 1 mass % of a water-soluble polymer comprising acrylic acid or methacrylic acid as a constitutional unit,
(C) 1 to 30 mass % of a hydrocarbon oil having a viscosity of 15 mPa·s or lower at 30° C.,
(D) 60 to 95 mass % of water, and
(E) 0.49 mass % or less of a nonionic surfactant having an HLB of larger than 9, wherein
the mass ratio of the component (B) to the component (A), (B)/(A) is from 0.0001 to 0.1, and the mass ratio between the component (A) and the component (C), (A)/((A)+(C)) is from 0.05 to 0.9.

The present invention also relates to a skin cleansing sheet comprising a nonwoven having a layered structure comprising a first layer and two second layers respectively disposed on surfaces of the first layer, and an O/W emulsion having a viscosity of from 200 to 15,000 mPa·s at 30° C. as an impregnating solution, wherein the ratio of the density of the first layer to the density of the second layers, (the density of the first layer/the density of the second layers) in the nonwoven is 1.05 or more, and the ratio of the thickness of the first layer to the thickness of one of the second layers, (the thickness of the first layer/the thickness of one of the second layers), in the nonwoven is from 0.6 to 1.5.

BRIEF DESCRIPTION OF DRAWING

FIG. 1 is a diagram showing one example of the cross section of the folded skin cleansing sheet of the present invention.

DETAILED DESCRIPTION OF THE INVENTION

Patent Literature 1 describes a cleansing cosmetic containing a dialkyl ether and a nonionic surfactant. Due to a large content of the nonionic surfactant, this cleansing cosmetic takes time to release oil from the product, slowly blends with traces of mascara, and leaves an oily feeling on the skin after cleansing. Patent Literature 2 describes a cleansing composition containing specific polyol and oil agent. This cleansing composition is not satisfactory in terms of an oily feeling of the skin after application. Patent Literature 3 describes a cleansing cosmetic containing a volatile oil, a nonvolatile oil, a hydrophilic nonionic surfactant, and a thickener. This cleansing cosmetic is not satisfactory in terms of a feeling of the skin after application.

As mentioned above, conventional cleansing agents have an insufficient cleansing power and also present problems associated with a feel in such a way that an oily feeling remains on the skin after application.

The present invention relates to a skin cleansing composition which can thoroughly remove stay-put makeup such as waterproof mascara and offers a favorable feel of the skin after application.

In addition, conventional cleansing sheets have an insufficient cleansing power and also present problems associated with stability. Particularly, skin cleansing sheets fail to thoroughly remove stay-put makeup and present problems associated with a feel when the skin is wiped or with stability.

The present invention relates to a skin cleansing sheet which can thoroughly remove stay-put makeup such as waterproof mascara and is excellent in a feel when the skin is wiped and in stability.

The present inventors have found that a skin cleansing composition which can thoroughly remove even stay-put makeup such as waterproof mascara, offers a soft and bouncy feeling of the skin after application, and sustains this feeling can be obtained by using an ether oil in a liquid state and a specific water-soluble polymer, and a hydrocarbon oil in combination at specific ratios. The soft and bouncy feeling of the skin means that the skin after application feels attracted to fingers without slipping, when touched with the fingers.

The present inventors have also found that a skin cleansing sheet which solves the problems described above can be obtained by the impregnation of a nonwoven having a layered structure differing in density with an O/W emulsion having a specific viscosity.

The skin cleansing composition of the present invention produces a high cleansing power against even stay-put makeup such as waterproof mascara, offers a fresh feel without an oily feeling, a soft and bouncy feeling of the skin after application, and a moist feeling, and sustains this feel.

The skin cleansing sheet of the present invention has a high cleansing power against even stay-put makeup such as waterproof mascara, offers a fresh feel, and is excellent in the thick feeling, softness, and smoothness of the sheet. In addition, the skin cleansing sheet also has favorable stability.

The ether oil as the component (A) used in the skin cleansing composition of the present invention is in a liquid state at 25° C. The liquid state refers to a state having fluidity at 25° C. and represents that the viscosity at 25° C. is 10,000 mPa·s or lower, preferably 50 mPa·s or lower, more preferably 15 mPa·s or lower.

The ether oil in a liquid state as the component (A) is preferably a dialkyl ether having two alkyl groups each having 16 or less of carbon atom, more preferably a dialkyl ether having two alkyl groups each having 8 or less of carbon atom. In the dialkyl ether, the two alkyl groups may be the same or different.

More specific examples thereof include dioctyl ether, cetyl-1,3-dimethyl butyl ether, dihexyl ether, and dilauryl ether. Of them, cetyl-1,3-dimethyl butyl ether and dioctyl ether are preferred, and dioctyl ether is more preferred, from the viewpoint of a high cleansing power and the absence of an oily feeling.

The component (A) can be used alone or in combination of two or more thereof. The content of the component (A) in the total composition is 0.1 mass % or more, preferably 0.5 mass % or more, more preferably 1 mass % or more, and is 25 mass % or less, preferably 10 mass % or less, more preferably 6 mass % or less, from the viewpoint of a cleansing power, a fresh feeling, and a moist feeling. The content of the component (A) in the total composition is from 0.1 to 25 mass %, preferably from 0.5 to 10 mass %, more preferably from 1 to 6 mass %.

The water-soluble polymer as the component (B) comprises acrylic acid or methacrylic acid as a constituent and is a water-soluble polymer comprising a constitutional unit derived from acrylic acid or methacrylic acid.

The water-soluble polymer comprising acrylic acid or methacrylic acid as a constitutional unit is synthesized with acrylic acid or methacrylic acid as a monomer. Examples thereof include a carboxyvinyl polymer and an acrylic acid/alkyl methacrylate copolymer. Of them, an acrylic acid/alkyl methacrylate copolymer is preferred, and a copolymer of acrylic acid and alkyl methacrylate having 10 to 30 of carbon atom ((acrylic acid/alkyl acrylate (C10-30)) copolymer) is more preferred, from the viewpoint of stability after preservation. Examples of commercially available products include PEMULEN TR-1, PEMULEN TR-2, and CARBOPOL ETD2020 (all manufactured by Lubrizol Advanced Materials, Inc.).

The water-soluble polymer comprising acrylic acid or methacrylic acid as a constitutional unit as the component (B) is preferably used after neutralization of the whole or a portion of the acrylic acid or methacrylic acid units using an alkali agent. The alkali agent for neutralization is not limited as long as the alkali agent can be ordinarily added to cosmetics. For example, potassium hydroxide, sodium hydroxide and the like can be used. The alkali agent can be used alone or in combination of two or more thereof. It is preferably contained at 0.0012 mass % or more and 0.4 mass % or less in the skin cleansing composition of the present invention. It is preferable to adjust the pH of the skin cleansing composition of the present invention to from 5 to 9, more preferably from 5.5 to 8.

The component (B) can be used alone or in combination of two or more thereof. The content of the component (B) in the total composition is 0.003 mass % or more, preferably 0.01 mass % or more, and more preferably 0.05 mass % or more, and is 1 mass % or less, preferably 0.5 mass % or less, and more preferably 0.1 mass % or less, from the viewpoint of a cleansing power, a fresh feeling, a moist feeling, and stability. The content of the component (B) in the total composition is from 0.003 to 1 mass %, preferably from 0.01 to 0.5 mass %, more preferably from 0.05 to 0.1 mass %.

In the present invention, the mass ratio of the component (B) to the component (A), (B)/(A) is preferably 0.0001 or more, more preferably 0.001 or more, and further more preferably 0.01 or more, and is preferably 0.1 or less, more preferably 0.085 or less, and further more preferably 0.07 or less, from the viewpoint of a cleansing power, a fresh feeling, a soft and bouncy feeling of the skin after application, a moist feeling, and stability. The mass ratio of the component (B) to the component (A), (B)/(A) is preferably from 0.0001 to 0.1, more preferably from 0.001 to 0.085, further more preferably 0.01 to 0.07.

The hydrocarbon oil as the component (C) used in the present invention has a viscosity of 15 mPa·s or lower, preferably from 1 to 10 mPa·s, at 30° C. from the viewpoint of a fresh feeling.

In this context, the viscosity is measured using a BM-type viscometer (manufactured by Tokimec, Inc., measurement conditions: rotor No. 1, 60 rpm, 1 min.).

Examples of the hydrocarbon oil as the component (C) include isododecane, isohexadecane, and hydrogenated polyisobutene. Isododecane is preferred from the viewpoint of a cleansing power and an excellent oil-free feeling.

The component (C) can be used alone or in combination of two or more thereof. The content of the component (C) in the total composition is 1 mass % or more, preferably 5 mass % or more, and more preferably 8 mass % or more, and is 30 mass % or less, preferably 25 mass % or less, and more preferably 15 mass % or less, from the viewpoint of a cleansing power and a fresh feeling. The content of the component (C) in the total composition is from 1 to 30 mass %, preferably from 5 to 25 mass %, more preferably from 8 to 15 mass %.

In the present invention, the mass ratio between the component (A) and the component (C), (A)/((A)+(C)) is 0.05 or more, preferably 0.08 or more, and more preferably 0.1 or more, and is 0.9 or less, preferably 0.8 or less, more preferably 0.4 or less, from the viewpoint of a high cleansing power, a soft and bouncy feeling of the skin after application, and the prevention of sliminess of the skin after application. The mass ratio between the component (A) and the component (C), (A)/((A)+(C)) is from 0.05 to 0.9, preferably from 0.08 to 0.8, more preferably from 0.1 to 0.4.

The water as the component (D) balances the components. The content of the component (D) in the total composition is 60 mass % or More, preferably 65 mass % or more, more preferably 70 mass % or more, and is 95 mass % or less, preferably 90 mass % or less, more preferably 85 mass % or less, from the viewpoint of a fresh feeling. The content of the component (D) in the total composition is from 60 to 95 mass %, preferably from 65 to 90 mass %, more preferably from 70 to 85 mass %.

In the present invention, the mass ratio of the component (A) to the component (D), (A)/(D) is preferably 0.001 or more, more preferably 0.01 or more, and further more preferably 0.02 or more, and is preferably 0.45 or less, more preferably 0.25 or less, further more preferably 0.15 or less, from the viewpoint of rendering the skin oil-free feeling after application. The mass ratio of the component (A) to the component (D), (A)/(D), is preferably from 0.001 to 0.45, more preferably from 0.01 to 0.25, further more preferably from 0.02 to 0.15.

In the present invention, the mass ratio of the component (B) to the component (D), (B)/(D) is preferably 0.000035 or more, more preferably 0.0001 or more, further more preferably 0.0005 or more, and is preferably 0.015 or less, more preferably 0.01 or less, further more preferably 0.005 or less, from the viewpoint of facilitating spreading the component (B) in water, maintaining the stability of an O/W emulsion, and a stronger soft and bouncy feeling of the skin after wiping. The mass ratio of the component (B) to the component (D), (B)/(D) is preferably from 0.000035 to 0.015, more preferably from 0.0001 to 0.01, further more preferably from 0.0005 to 0.005.

The skin cleansing composition of the present invention can further comprise (E) a nonionic surfactant having an HLB larger than 9. The (E) nonionic surfactant can accelerate the release of oil in an emulsion upon application, allows the composition to rapidly exert cleansing performance, and can produce better stability.

The nonionic surfactant has an HLB preferably from 9 to 20, more preferably from 10 to 17.

The HLB refers to an index which indicates a hydrophile-lipophile balance. In the present invention, a value calculated using the following expression of Oda, Teramura, etc. is used:

$$HLB\ value = \frac{\Sigma\ \text{Inorganic value}}{\Sigma\ \text{Organic value}} \times 10$$

Examples of the nonionic surfactant include polyglycerin fatty acid ester, polyethylene glycol fatty acid ester, polyoxyethylene glycerin fatty acid ester, propylene glycol fatty acid ester, polyoxyethylene polyoxypropylene glycol, sorbitan fatty acid ester, polyoxyethylene sorbitan fatty acid ester, polyoxyethylene sorbitol fatty acid ester, polyoxyethylene castor oil, polyoxyethylene hydrogenated castor oil, polyoxyethylene hydrogenated castor oil fatty acid ester, polyoxypropylene polyglyceryl ether, polyalkyl glyceryl ether, polyoxyethylene alkyl ether, polyoxyethylene alkyl ether fatty acid ester, sucrose fatty acid ester, alkyl polyglucoside, and (poly)alkyl glyceryl ether.

The nonionic surfactant is preferably polyglycerin fatty acid ester, polyethylene glycol fatty acid ester, polyoxyethylene glycerin fatty acid ester, polyoxyethylene sorbitan fatty acid ester, alkyl polyglucoside, or (poly)alkyl glyceryl ether, from the viewpoint of a cleansing power.

The nonionic surfactant can be used alone or in combination of two or more thereof. The content of the nonionic surfactant in the total composition is preferably 0.0001 mass % or more, more preferably 0.005 mass % or more, further more preferably 0.01 mass % or more, and is preferably 3 mass % or less, more preferably 0.49 mass % or less, further more preferably 0.049 mass % or less, from the viewpoint of a cleansing power, low stickiness, and stability. The content of the nonionic surfactant in the total composition is preferably 0.0001 to 3 mass %, more preferably 0.005 to 0.49 mass %, further more preferably 0.01 to 0.049 mass %.

In the present invention, the mass ratio of the component (E) to whole oil agents ((E)/whole oil agents) is preferably 0.01 or less, more preferably 0.008 or less, further more preferably 0.005 or less, from the viewpoint of stability.

In the present invention, the mass ratio of the component (A) to the component (E), (A)/(E) is preferably 0.1 or more, more preferably 1 or more, further more preferably 40 or more, and is preferably 200,000 or less, more preferably 600 or less, further more preferably 200 or less, from the viewpoint of a cleansing power, stability, and reduction in a slimy feeling of the skin after application. The mass ratio of the component (A) to the component (E), (A)/(E) is preferably from 0.1 to 200,000, more preferably from 1 to 600, further more preferably from 40 to 200.

The cleansing composition of the present invention can further comprise (F) a water-soluble solvent. The water-soluble solvent can produce a moist feeling.

Specific examples of the component (F) include polyhydric alcohols, polyglycerin, polyethylene glycol, polypropylene glycol, glyceryl ethers having an alkylene group added to glycerin, and sugars.

More specifically, examples of the polyhydric alcohols include ethylene glycol, propylene glycol, isoprene glycol, 1,3-butylene glycol, hexylene glycol, trimethylolpropane, and glycerin. Of them, propylene glycol, isoprene glycol, 1,3-butylene glycol, hexylene glycol, and glycerin are preferred. 1,3-Butylene glycol, propylene glycol, isoprene glycol, and glycerin are more preferred from the viewpoint of a moist feeling of the skin after rinsing or after wiping.

Examples of the polyglycerin, the polyethylene glycol, and the polypropylene glycol include polyglycerin having a molecular weight of 2,000 or smaller, polyethylene glycol having a molecular weight of 10,000 or smaller, and polypropylene glycol having a molecular weight of 1,000 or smaller. Of them, diglycerin, polyethylene glycol 200, polyethylene glycol 400, polyethylene glycol 1000, polyethylene glycol 1540, dipropylene glycol, polypropylene glycol (3), and polypropylene glycol (7) are preferred from the viewpoint of a moist feeling of the skin after rinsing or after wiping.

Examples of the glyceryl ethers having an alkylene group added to glycerin include polyoxypropylene diglyceryl ether, polyoxypropylene glyceryl ether, and polyoxybutylene polyoxyethylene polyoxypropylene glyceryl ether. Of them, polyoxypropylene (9) diglyceryl ether, polyoxypropylene (14) diglyceryl ether, and polyoxybutylene polyoxyethylene polyoxypropylene glyceryl ether (3B.O.)(8E.O.)(5P.O.) are preferred from the viewpoint of low stickiness.

Examples of the sugars include sorbitol, erythritol, pentaerythritol, methyl glucoside, ethyl glucoside, polyoxyethylene methyl glucoside, and polyoxypropylene methyl glucoside. Alkyl glucoside having 2 or less of carbon atom in the alkyl chain is preferred. Of them, methyl glucoside, ethyl glucoside, polyoxyethylene methyl glucoside, and polyoxypropylene methyl glucoside are preferred. Polyoxyethylene methyl glucoside and polyoxypropylene methyl glucoside are more preferred from the viewpoint of a moist feeling of the skin after rinsing or after wiping.

The component (F) can be used alone or in combination of two or more thereof. The content of the component (F) in the total composition is preferably 1 mass % or more, more preferably 3 mass % or more, further more preferably 5 mass % or more, and is preferably 35 mass % or less, more preferably 25 mass % or less, further more preferably 15 mass % or less, from the viewpoint of offering a moist feeling and low stickiness. The content of the component (F) in the total composition is preferably from 1 to 35 mass %, more preferably from 3 to 25 mass %, further more preferably from 5 to 15 mass %.

In the present invention, the mass ratio of the component (A) to the component (F), (A)/(F) is preferably 0.003 or more, more preferably 0.01 or more, further more preferably 0.1 or more, and is preferably 25 mass % or less, more preferably 10 or less, further more preferably 1 or less, from the viewpoint of offering a moist feeling and low stickiness. The mass ratio of the component (A) to the component (F), (A)/(F) is preferably from 0.003 to 25, more preferably from 0.01 to 10, further more preferably from 0.1 to 1.

In the present invention, the mass ratio of the component (B) to the component (F), (B)/(F) is preferably 0.0001 or more, more preferably 0.001 or more, further more preferably 0.005 or more, and is preferably 1 or less, more preferably 0.1 or less, further more preferably 0.02 or less, from the viewpoint of offering a moist feeling and low stickiness. The mass ratio of the component (B) to the component (F), (B)/(F) is preferably from 0.0001 to 1, more preferably from 0.001 to 0.1, further more preferably from 0.005 to 0.02.

The skin cleansing composition of the present invention can further comprise (G) a nonionic water-soluble polymer comprising cellulose as a constitutional unit. The nonionic water-soluble polymer can further reduce an oily feeling.

Examples of such a nonionic water-soluble polymer include: alkylcelluloses such as methylcellulose and ethylcellulose; and hydroxyalkylcelluloses such as hydroxyethylcellulose, hydroxypropylcellulose, and hydroxypropylmethylcellulose.

Of them, a hydroxyalkylcellulose is preferred, and hydroxyethylcellulose is more preferred, from the viewpoint of a high cleansing power and the absence of an oily feeling.

The nonionic water-soluble polymer as the component (G) has a molecular weight of preferably from 50,000 to 3,000,000, more preferably from 100,000 to 1,300,000, from the viewpoint of a cleansing power and the absence of an oily feeling.

The component (G) can be used alone or in combination of two or more thereof. The content of the component (G) in the total composition is 0.01 mass % or more, preferably 0.05 mass % or more, more preferably 0.075 mass % or more, and is 5 mass % or less, preferably 2 mass % or less, more preferably 0.5 mass % or less, from the viewpoint of a cleansing power, the absence of an oily feeling, and a moist feeling. The content of the component (G) in the total composition is 0.01 to 5 mass %, preferably from 0.05 to 2 mass %, more preferably from 0.075 to 0.5 mass %.

In the skin cleansing composition of the present invention, the content of an anionic surfactant in the total composition is preferably less than 5 mass %, more preferably 3 mass % or less, further more preferably 1 mass % or less, still further more preferably 0.1 mass % or less, still further more preferably zero, from the viewpoint of a cleansing power and low stickiness.

The skin cleansing composition of the present invention can comprise, in addition to the components described above, a component used in ordinary cleansing compositions without inhibiting the effects of the present invention. The skin cleansing composition of the present invention can comprise, for example, an oil agent other than the components (A) and (C), a polymer other than the components (B) and (G), a cationic surfactant, an amphoteric surfactant, a bactericide, an anti-inflammatory agent, an antiseptic, a chelating agent, a salt, a pearling agent, a fragrance, a cooling agent, a dye, an ultraviolet absorber, an antioxidant, and a plant extract.

Examples of the oil agent other than the components (A) and (C) include hydrocarbon oils, such as liquid paraffin, having a viscosity exceeding 30 mPa·s at 30° C. The oil agent other than the components (A) and (C) can be used alone or in combination of two or more thereof. The content of the oil agent other than the components (A) and (C) in the total composition is preferably 0.01 mass % or more, and is preferably 20 mass % or less, more preferably 10 mass % or less, further more preferably 5 mass % or less, still further more preferably 1 mass % or less.

Examples of the polymer other than the components (B) and (G) include sodium hyaluronate.

The skin cleansing composition of the present invention is preferably free from the cationic surfactant and the amphoteric surfactant, except when these surfactants are irreversibly mixed thereinto without inhibiting the effects of the present invention.

The skin cleansing composition of the present invention can be produced according to a conventional method by mixing the components to be contained. The skin cleansing composition comprising a starting material which is solid at normal temperature can be produced by thermally melting the solid material or dissolving the solid material in other components and then uniformly mixing all components.

The skin cleansing composition of the present invention has a viscosity of preferably from 200 to 10,000 mPa·s, more preferably from 500 to 4,000 mPa·s, at 25° C. from the viewpoint of a cleansing power, a fresh feeling, and stability.

When the skin cleansing composition of the present invention is prepared into an O/W emulsion, the average particle size of the emulsified particles is preferably from 1 to 30 μm, more preferably from 2 to 20 μm, further more preferably from 3 to 15 μm, from the viewpoint of a cleansing power, stability, and a moist feeling.

The skin cleansing composition of the present invention is suitable as, for example, a facial wash or a cleansing agent and is more preferably a cleansing agent. Also, the skin cleansing composition of the present invention is preferably used for cleansing a makeup cosmetic applied on the face.

The skin cleansing composition of the present invention can be used by, for example, a method of applying the composition on a cotton etc. and wiping the skin with the cotton etc., where the composition may be used as it is or after shaking it up till uniform if it is a separated composition; a method of wiping with a cotton etc. after applying the composition to the skin with a palm; a method of washing off after applying the composition to the skin with a palm; a method of washing after applying the composition to a cotton etc. and spreading the composition over the skin; a method of washing off the composition after wiping the skin according to any one of the above methods. The composition can be also used in a form in which a sheet is impregnated with the composition, which is most preferable.

A sheet can be impregnated with the skin cleansing composition of the present invention to prepare a skin cleansing sheet. A nonwoven is preferably used as the sheet. A nonwoven which is made of fibers having a cellulose content of 30 mass % or more and has a density of from 0.05 to 0.3 g/cm$^3$ is preferred from the viewpoint of a cleansing power, stability, smoothness, and the sustention of a moist feeling after cleansing.

Specific examples of the cellulose fibers include cotton and rayon. Cotton is preferred from the viewpoint of smooth texture. The nonwoven is preferably obtained by a hydroentangling method from the viewpoint of a feel of the skin.

The cellulose fibers may be mixed with hydrophobic fibers in order to modify the sheet. Examples of the hydrophobic fibers include polyester fibers such as polyethylene terephthalate (PET), polybutylene terephthalate (PBT), polypropylene (PP), and polyethylene (PE).

The nonwoven preferably has a relatively high density for retaining the impregnating skin cleansing composition and preventing its movement in the sheet material. The density of the nonwoven is preferably 0.05 g/cm$^3$ or larger from the viewpoint of preventing the solution from easily moving to a lower sheet by the gravity, and meanwhile, is preferably 0.3 g/cm$^3$ or smaller from the viewpoint of facilitating dampening the sheet with the impregnating solution and offering a soft feel upon application of the sheet. The density of the nonwoven is more preferably from 0.075 to 0.25 g/cm$^3$ for preventing the movement of the solution and balancing feelings upon application.

The average basis weight (mass per unit area) of the nonwoven is preferably 40 g/m$^2$ or larger from the viewpoint of being convenient without twisting upon wiping and preventing traces from being transferred to the backside, and is preferably 100 g/m$^2$ or smaller from the viewpoint of preventing laminated fabrics from being bulky and offering a supple feel. The average basis weight of the nonwoven is more preferably from 50 to 80 g/m$^2$ for manageability upon application and the moderate bulkiness of laminated fabrics.

The nonwoven may be a sheet material in which two or more nonwovens are layered or laminated. A nonwoven having a three-layer structure is more preferred.

The form of the nonwoven is preferably a shape, a size, and a thickness which confer easiness to use by hand. Examples thereof include square, rectangular, round, and ellipsoidal shapes having one side or diameter on the order of from 5 to 20 cm. The thickness is preferably on the order of from 0.2 to 0.6 mm.

The rate of impregnation of the nonwoven with the skin cleansing composition is preferably from 50 to 1,500%, more preferably from 300 to 700%, from the viewpoint of a cleansing power, a fresh feeling, smoothness, stability, and usability.

For the impregnation of the sheet with the skin cleansing composition, for example, the skin cleansing composition can be applied to the nonwoven by dropwise addition from a nozzle or sprayed onto the nonwoven and then left so that the sheet material is sufficiently impregnated with the skin cleansing composition to produce a skin cleansing sheet.

One or two- or more ply skin cleansing sheet can usually be sealed in a bag for use. Upon application, the bag is opened, and at least one cleansing sheet is taken out of the bag and used such that the sheet is pressed against a site where a makeup cosmetic is to be removed, regardless of oil-based makeup cosmetics or water-based makeup cosmetics, to wipe off the makeup cosmetic. As a result, a high cleansing power can be exerted against even stay-put makeup such as waterproof mascara.

Even if the skin cleansing sheet of the present invention is preserved in the form of laminated sheets for a long period, the impregnating solution is prevented from moving upward or downward. In addition, its composition is not altered. The quality can therefore be stably maintained.

The nonwoven used in the skin cleansing sheet of the present invention has a layered structure and comprises a first layer (intermediate layer) and two second layers (surface layers) respectively disposed on surfaces thereof. The ratio of the density of the first layer to the density of the second layers, (the density of the first layer/the density of the second layers), in the nonwoven is 1.05 or more. The ratio of the thickness of the first layer to the thickness of one of the second layers, (the thickness of the first layer/the thickness of one of the second layers), in the nonwoven is from 0.6 to 1.5. The skin cleansing sheet comprises an O/W emulsion having a viscosity of from 200 to 15,000 mPa·s at 30° C. as an impregnating solution.

In the case of a skin cleansing sheet in which a nonwoven having a high density is used, the nonwoven usually offers a hard feel and retains a small amount of the impregnating solution due to densely compacted fibers. This nonwoven, however, is elastic upon wiping and permits thorough wiping. For people who want to gently wipe the skin, such a nonwoven may not be preferred due to a strong touch to the skin resulting from the hard nonwoven and a small amount of the cleansing solution.

Accordingly, a skin cleansing sheet in which a nonwoven having a low density is used is possible. Since the nonwoven having a low density has sparse fibers, the nonwoven itself is soft and deformed and permits smooth wiping. Due to the sparse and easily deformable fibers, however, the impregnating solution tends to ooze when laminated sheets are preserved. The quality of such a skin cleansing sheet is often difficult to stably maintain over time. When this sheet is picked up by hand or pressed against the skin for wiping, the impregnating solution may overflow (and run out of the sheet) so that the cleansing solution is insufficiently applied to between the skin and the sheet upon wiping operation.

Accordingly, as in the skin cleansing sheet of the present invention, the combination of two nonwovens (fiber webs) differing in density can reduce the oozing or overflow of the impregnating solution and maintain the stability of the quality of laminated sheets, and the surface layers each composed of a nonwoven having a low density can produce a high cleansing power and a fresh feeling and produce the thick feeling, softness, and smoothness of the sheet. In this context, the "thick feeling of the sheet" refers to a feeling from the sheet which is deformed upon wiping to give a gentle touch to the skin.

The skin cleansing sheet of the present invention stably maintains its quality when laminated, presumably because low-density nonwovens are used as the surface layers and combined with a high-density nonwoven as the intermediate layer. When the stability of laminated skin cleansing sheets is confirmed over time, in a sheet in which only a low-density nonwoven is impregnated with an impregnating solution, the impregnating solution oozes from an upper layer to a lower layer to decrease the amount of the impregnating solution retained in the sheet. By contrast, in the case of the skin cleansing sheet of the present invention, the first layer of the high-density nonwoven is sandwiched between the second layers (surface layers) of the low-density nonwovens. Since the high-density nonwoven has densely packed fibers, the impregnating solution seeking to ooze from the low-density nonwovens is less likely to pass through the high-density nonwoven. Furthermore, since the skin cleansing sheet of the present invention has a structure in which the density gradient is reversed, the impregnating solution is less likely to move downward. As a result, the quality can be stably maintained.

The ratio of the density of the first layer to the density of the second layers, (the density of the first layer/the density of the second layers), in the nonwoven is 1.05 or more, preferably 1.1 or more, more preferably 1.15 or more, and is 2.3 or less, preferably 2.0 or less, more preferably 1.7 or less. The ratio of the density of the first layer to the density of the second layers, (the density of the first layer/the density of the second layers), in the nonwoven is from 1.05 to 2.3, preferably from 1.1 to 2.0, more preferably from 1.15 to 1.7. The density is calculated from the basis weight and the thickness (Basis weight/Thickness). In this context, the density of the first layer and the density of the second layers refer to the density of each layer alone before preparation of a nonwoven by the combination of the first layer and the second layers.

The porosity of each layer is measured by the image analysis of area S1 occupied by fibers in arbitrary area S0 (of a rectangular site) of each layer from a magnified photograph of the cross section of the sheet by use of an electron microscope, and calculated from density ρ of the fibers themselves (calculation expression of the porosity of each layer: ρ×S1/S0).

The porosity of pulp is preferably from 0.01 to 0.2, more preferably from 0.02 to 0.1, and the porosity of cotton is preferably from 0.001 to 0.04, more preferably from 0.002 to 0.02.

In the nonwoven, the density of the first layer (intermediate layer) is preferably 0.08 g/cm$^3$ or larger, more preferably 0.1 g/cm$^3$ or larger, further more preferably 0.12 g/cm$^3$ or larger, and is preferably 0.3 g/cm$^3$ or smaller, more preferably 0.2 g/cm$^3$ or smaller, further more preferably 0.18 g/cm$^3$ or smaller. The density of the first layer (intermediate layer) is preferably 0.08 to 0.3 g/cm$^3$, more preferably from 0.1 to 0.2 g/cm$^3$, further more preferably from 0.12 to 0.18 g/cm$^3$.

In the nonwoven, the density of the second layers (surface layers) is preferably 0.04 g/cm$^3$ or larger, more preferably 0.06 g/cm$^3$ or larger, further more preferably 0.08 g/cm$^3$ or larger, and is preferably 0.27 g/cm$^3$ or smaller, more preferably 0.18 g/cm$^3$ or smaller, further more preferably 0.16 g/cm$^3$ or smaller. The density of the second layers (surface layers) is preferably from 0.04 to 0.27 g/cm$^3$, more preferably from 0.06 to 0.18 g/cm$^3$, further more preferably from 0.08 to 0.16 g/cm$^3$.

In the nonwoven, the first layer is preferably constituted by fibers selected from the group consisting of hydrophilic fibers of cellulose such as pulp, cotton, rayon, cupra, and lyocell from the viewpoint of the absence of twisting when the skin is wiped, elasticity upon wiping, and the retention stability of the impregnating solution. Pulp is more preferred because a density at which the impregnating solution is less likely to pass through the first layer is easily obtained.

The fiber thickness of the first layer is preferably from 5 to 100 μm, more preferably from 10 to 40 μm, from the viewpoint of the absence of twisting when the skin is wiped.

The basis weight of the first layer in the nonwoven is preferably from 10 to 80 g/m$^2$ from the viewpoint of the absence of twisting when the skin is wiped, and the retention stability of the impregnating solution. The basis weight of the first layer in the nonwoven is more preferably from 15 to 30 g/m$^2$ from the viewpoint of conferring moderate elasticity upon wiping.

The thickness of the first layer in the nonwoven is preferably from 50 to 700 μm, more preferably from 100 to 300 μm, from the viewpoint of formation favorable enough not to cause the pass-through of the solution, and the retention stability of the impregnating solution.

In the present invention, the thickness of the whole sheet is indicated by an average value (mm) of thicknesses determined by sampling two 200 mm×200 mm pieces from the nonwoven and measuring 3 points using a dial gauge under a pressing load of 1.96 kPa (20 g/cm$^2$). The thickness of each layer for calculating the density is indicated by an average value of results of measurement at 3 sites using a magnified photograph.

In contrast, the second layers are preferably constituted by fibers selected from the group consisting of cotton, rayon, lyocell, PET, and nylon from the viewpoint of low friction when the skin is wiped (because the nonwoven is soft and the impregnating solution is prevented from overflowing before wiping), a smooth feel, and a cleansing power. Also, the second layers are preferably rich in hydrophilic fibers from the viewpoint of preventing the overflow of the impregnating solution. Fibers at least comprising cotton are preferred, and cotton is more preferred, from the viewpoint of a gentle touch to the skin by virtue of the nonwoven structure in which deformation attributed to twisted fibers is easily canceled.

The fiber thickness of the second layers is preferably from 1 to 80 μm, more preferably from 10 to 30 μm, from the viewpoint of the absence of friction when the skin is wiped, a soft and smooth feel, and a cleansing power.

The basis weight of the second layers in the nonwoven is preferably from 10 to 80 g/m$^2$, more preferably from 10 to 40 g/m$^2$, in sum of the two second layers, from the viewpoint of little likelihood of twisting when the skin is wiped, formation, and the impregnation properties of the cleansing solution.

The thickness of each of the second layers in the nonwoven is preferably from 50 to 500 μm, more preferably from 100 to 300 μm, from the viewpoint of softness, stability, and the impregnation properties of the cleansing solution. The thickness of the second layers can be determined by subtracting the thickness of the first layer from the thickness of the whole sheet ((Thickness of the whole sheet)−(Thickness of the first layer)). The thickness of one of the second layers can be estimated to be half of the calculated thickness of the second layers, when the two second layers produced have equal thicknesses.

The two second layers may be the same or different.

The ratio of the thickness of the first layer to the thickness of one of the second layers, (the thickness of the first layer/the thickness of one of the second layers), in the nonwoven is preferably from 0.2 to 5.0, more preferably from 0.4 to 2.5, further more preferably from 0.5 to 2.0, still further more preferably from 0.6 to 1.5, from the viewpoint of a gentle feeling from wiping and stability.

The nonwoven has the second layers (surface layers) respectively disposed on both surfaces of the first layer (intermediate layer) and preferably has a three-layer structure. Such a nonwoven is produced through the complexation of these layers by hydroentangling or thermal embossing.

In the nonwoven, the fibers of the first layer and the second layers are preferably interlaced in the boundaries between the first layer and the second layers from the viewpoint of little likelihood of twisting.

The average fiber diameter of the fibers constituting the nonwoven is preferably from 1 to 50 μm, more preferably from 5 to 30 μm, from the viewpoint of low friction when the skin is wiped, a soft and smooth feel, and a cleansing power.

A mixed layer of the fibers of the first layer and each of the second layers may be formed in more boundaries between the first layer and the second layers formed through complexation by a hydroentangling method. In this case, the oozing or overflow of the impregnating solution is much less likely to occur. The mixed layer of the fibers is preferably formed between the first layer and each of the second layers such that the thickness of the mixed layer on one side accounts for 5 to 40% of the total thickness of the sheet comprising the first layer and the two second layers. The thickness of the mixed layer on one side more preferably accounts for from 10 to 35% of the total thickness of the sheet comprising the first layer and the two second layers from the viewpoint of a soft and smooth feel on the skin upon wiping of the skin, the easy distribution of the impregnating solution to between the skin and the sheet upon wiping, reduction in friction, and cleansing properties.

The mixed layer preferably assumes a fiber gradation structure in which more fibers of the first layer reside on the first layer side while more fibers of the second layers reside on the second layer side, from the viewpoint of distributing a moderate amount of the impregnating solution to between the skin and the sheet to enhance cleansing properties.

The thicknesses of the first layer and the second layers mentioned above refer to the thickness of each single layer before production. The thickness of the mixed layer is included in the total thickness of the first layer and each of the second layers.

The percentage of the mixed layer of the fibers is determined by measuring the thickness of a site where the fibers of the first layer and each second layer are mixed with each other as the thickness of the mixed layer from a magnified photograph of the cross section of the sheet, and calculating the percentage from a half value of the thickness of the whole sheet at the measurement site of the mixed layer of the fibers in the magnified photograph of the cross section (Mixed layer thickness/Half value of the sheet thickness× 100(%)).

For the formation of the mixed layer, it is considered that water jets are dispersed by bouncing off the first layer by hydroentangling without penetrating the high-density first layer, and thereby spread in a wide range to form a layer. In such a case, the conjugation of the sheet tends to be weakened. Preferably, after hydroentangling of the first and second surfaces, water jets are applied to either surface under strong water jet conditions. The water jets under strong conditions also have the advantage that the water jets are less likely to penetrate the first layer, because the density of the whole sheet is increased in this state.

It is also preferred to carry out dispersed embossing treatments to improve partial complexation and suppress the peeling of the sheet attributed to a relief structure.

For the sheet of the present invention, a relief structure is preferably imparted to both surfaces of the sheet.

In the complexation of the sheet, a very small surface relief structure by hydroentangling or a relatively large relief structure by embossing can be conferred. In such a case, the contact between the inner surfaces of sheets can be reduced by the size or shape of the relief structure. Thus, the movement of the solution between the inner surfaces can be further reduced. The relief form of the sheet is preferably a form in which linearly asymmetric shapes, such as ellipsoid, rectangular, or streaky shapes, which are less likely to overlap between the inner surfaces are formed.

When the cross section of the sheet has partial protrusions, the amount of the impregnating solution is partially increased. The inner surfaces of sheets come in contact with each other at this site with the increased amount of the impregnating solution. The solution moves, albeit very slightly, from the other portions of the sheet to this site so that the amount of the solution becomes relatively low in the other portions compared with the protrusions. In the case of a folded sheet, if the oozing of the solution occurs even in a small amount in the upper inner surface and the lower inner surface on the inner surface side of the folded sheet, the amount of the solution retained differs between the upper inner surface and the lower inner surface near the folding site. As a result, the solution is soaked up by virtue of the capillary action of the high-density portion of the second layer in the inner surfaces of the folding site to further enhance the effect of reducing the relative difference in the amount of the solution.

The total basis weight of the nonwoven is preferably from 20 to 150 g/m$^2$, more preferably from 35 to 80 g/m$^2$, from the viewpoint of little likelihood of twisting when the skin is wiped, the impregnation property of solution, and stability.

In the nonwoven, the ratio of the basis weight of the first layer to the basis weight of one of the second layers, (the basis weight of the first layer/the basis weight of one of the second layers), is preferably from 0.2 to 5.0, more preferably from 0.4 to 2.0, from the viewpoint of the easy oozing of the wiping solution when the skin is wiped, and a cleansing power.

The thickness of the nonwoven is preferably from 0.1 to 1.5 mm, and more preferably from 0.3 to 0.7 mm, from the viewpoint of softness, stability, and the impregnation properties of the cleansing solution.

The saturation water level in the nonwoven is preferably from 500 to 1,500%, more preferably from 750 to 1,000%, from the viewpoint of stability, a cleansing power, and the impregnation properties of the cleansing solution. The saturation water level is determined by a method which abides by JIS L 1913 Test methods for nonwovens (6.9.2 water retention). Specifically, nonwoven samples of 10 cm×10 cm in size are dipped in a container containing ion-exchange water for 5 minutes and then taken out of the container. Both ends of one side of each sample are anchored with tweezers and kept for 30 seconds. Then, the weights of the nonwoven samples impregnated with ion-exchange water are measured to calculate the saturation water level.

The ratio of the basis weight (g/m$^2$) of the second layers in the nonwoven to the viscosity (mPa·s) at 30° C. of the O/W emulsion mentioned later, (the basis weight of the second layers/the viscosity) is preferably from 0.007 to 0.7, more preferably from 0.01 to 0.15, from the viewpoint of stability, a cleansing power, and the impregnation properties of the cleansing solution.

For the nonwoven used in the present invention, preferably, pulp is used as the first layer, and cotton is used as the second layers, from the viewpoint of a smooth and natural feel of the skin when the skin is wiped, a cleansing power, softness, stability, and the impregnation properties of the cleansing solution. In this case, the mass ratio of cotton to all fibers, i.e., cotton/(cotton+pulp) is preferably from 0.3 to 0.95, more preferably from 0.5 to 0.6, from the viewpoint of low intensity upon wetting when the skin is wiped, the balance between gentle wiping and excellent stretchability, and stability.

In the present invention, the O/W emulsion with which the nonwoven as described above is impregnated has a viscosity of from 200 to 15,000 mPa·s, preferably from 500 to 3,000 mPa·s, at 30° C. This viscosity prevents the transfer of the impregnating solution from the upper side to the lower side when laminated sheets are preserved. Such a skin cleansing sheet is also excellent in smoothness upon wiping.

In this context, the viscosity is measured using a BM-type viscometer (manufactured by Tokimec, Inc., measurement conditions: rotor No. 2, 6 rpm, 1 min.).

The O/W emulsion can comprise (H) an ether oil which is in a liquid state at 25° C. The liquid state refers to a state having fluidity at 25° C. and represents that the viscosity at 25° C. is 10,000 mPa·s or lower, preferably 50 mPa·s or lower, more preferably 15 mPa·s or lower.

The ether oil in a liquid state as the component (H) is preferably a dialkyl ether having two alkyl groups each having 16 or less of carbon atom, more preferably a dialkyl ether having two alkyl groups each having 8 or less of carbon atom. In the dialkyl ether, the two alkyl groups may be the same or different.

More specific examples thereof include dioctyl ether, cetyl-1,3-dimethyl butyl ether, dihexyl ether, and dilauryl ether. Of them, cetyl-1,3-dimethyl butyl ether and dioctyl ether are preferred, and dioctyl ether is more preferred, from the viewpoint of a high cleansing power against oil-based mascara and the absence of an oily feeling.

The component (H) can be used alone or in combination of two or more thereof. The content of the component (H) in the total composition is preferably 0.1 mass % or more, more preferably 0.5 mass % or more, further more preferably 1 mass % or more, and is preferably 25 mass % or less, more preferably 10 mass % or less, further more preferably 6 mass % or less, from the viewpoint of a cleansing power, a fresh feeling, and a moist feeling. The content of the component (H) in the total composition is preferably from 0.1 to 25 mass %, more preferably from 0.5 to 10 mass %, further more preferably from 1 to 6 mass %.

The O/W emulsion can further comprise a (I) a hydrocarbon oil having a viscosity of 30 mPa·s or lower, preferably from 1 to 10 mPa·s, at 30° C. In this context, the viscosity is measured using a BM-type viscometer (manufactured by Tokimec, Inc., measurement conditions: rotor No. 1, 60 rpm, 1 min.).

Examples of the hydrocarbon oil include isododecane, isohexadecane, and hydrogenated polyisobutene. Isododecane is preferred from the viewpoint of a cleansing power and an excellent feel without an oily feeling.

The component (I) can be used alone or in combination of two or more thereof. The content of the component (I) in the total composition is preferably 1 mass % or more, more preferably 5 mass % or more, further more preferably 10 mass % or more, and is preferably 50 mass % or less, more preferably 35 mass % or less, further more preferably 20 mass % or less, from the viewpoint of a cleansing power, a fresh feeling, and stability. The content of the hydrocarbon oil as the component (I) in the total composition is preferably from 1 to 50 mass %, more preferably from 5 to 35 mass %, further more preferably from 10 to 20 mass %.

The O/W emulsion can also comprise (J) a water-soluble polymer. The water-soluble polymer can produce a higher cleansing power.

The water-soluble polymer is preferably a nonionic water-soluble polymer comprising cellulose as a constitutional unit or a water-soluble polymer comprising acrylic acid or methacrylic acid as a constitutional unit (water-soluble polymer comprising a constitutional unit derived from acrylic acid or methacrylic acid), from the viewpoint of a cleansing power and stability.

Examples of the nonionic water-soluble polymer comprising cellulose as a constitutional unit include: alkylcelluloses such as methylcellulose and ethylcellulose; and hydroxyalkylcelluloses such as hydroxyethylcellulose, hydroxypropylcellulose, and hydroxypropylmethylcellulose.

Of them, a hydroxyalkylcellulose is preferred, and hydroxyethylcellulose is more preferred, from the viewpoint of a high cleansing power and the absence of an oily feeling.

The water-soluble polymer comprising acrylic acid or methacrylic acid as a constitutional unit is synthesized with acrylic acid or methacrylic acid as a monomer. Examples thereof include a carboxyvinyl polymer and an acrylic acid/alkyl methacrylate copolymer. Of them, an acrylic acid/alkyl methacrylate copolymer is preferred, and a copolymer of acrylic acid and alkyl methacrylate having from 10 to 30 of carbon atom ((acrylic acid/alkyl acrylate (C10-30)) copolymer) is more preferred, from the viewpoint of stability after preservation. Examples of commercially available products include PEMULEN TR-1, PEMULEN TR-2, and CARBOPOL ETD2020 (all manufactured by Lubrizol Advanced Materials, Inc.).

The water-soluble polymer comprising acrylic acid or methacrylic acid as a constitutional unit is preferably used after neutralization of the whole or a portion of the acrylic acid or methacrylic acid units using an alkali agent. The alkali agent for neutralization is not limited as long as the alkali agent can be added to ordinary cosmetics. For example, potassium hydroxide or sodium hydroxide can be used. The alkali agent can be used alone or in combination of two or more thereof and is preferably contained at 0.001 mass % or more and 0.4 mass % or less in the O/W emulsion to adjust the pH of the composition to preferably from 5 to 9, more preferably from 5.5 to 8.

The water-soluble polymer as the component (J) has a molecular weight of preferably from 50,000 to 5,000,000, more preferably from 100,000 to 4,000,000, from the viewpoint of a cleansing power, stability, and a fresh feeling.

The water-soluble polymer can be used alone or in combination of two or more thereof. The content of the water-soluble polymer in the total composition is preferably 0.01 mass % or more, more preferably 0.025 mass % or more, further more preferably 0.05 mass % or more, and is preferably 1 mass % or less, more preferably 0.7 mass % or less, further more preferably 0.3 mass % or less, from the viewpoint of a cleansing power, stability, impregnation properties, and a fresh feeling. The content of the water-soluble polymer in the total composition is preferably from 0.01 to 1 mass %, more preferably from 0.025 to 0.7 mass %, further more preferably from 0.05 to 0.3 mass %.

The mass ratio of the component (J) to the component (H), (J)/(H) in the O/W emulsion is preferably 0.001 or more, more preferably 0.004 or more, and further more preferably 0.01 or more, and is preferably 5 or less, more preferably 2.5 or less, and further more preferably 1 or less, from the viewpoint of a smooth feel remaining on the skin and the sustention of the smooth feel. The mass ratio of the component (J) to the component (H), (J)/(H) is preferably from 0.001 to 5, more preferably from 0.004 to 2.5, further more preferably from 0.01 to 1.

The O/W emulsion can also comprise (K) a water-soluble solvent. The water-soluble solvent can produce a moist feeling.

Specific examples of the component (K) include polyhydric alcohols, polyglycerin, polyethylene glycol, polypropylene glycol, glyceryl ethers having an alkylene group added to glycerin, and sugars.

More specifically, examples of the polyhydric alcohols include ethylene glycol, propylene glycol, isoprene glycol, 1,3-butylene glycol, hexylene glycol, trimethylolpropane, and glycerin. Of them, propylene glycol, isoprene glycol, 1,3-butylene glycol, hexylene glycol, and glycerin are preferred. 1,3-Butylene glycol, propylene glycol, isoprene glycol, and glycerin are more preferred from the viewpoint of a moist feeling of the skin after rinsing or after wiping.

Examples of the polyglycerin, the polyethylene glycol, and the polypropylene glycol include polyglycerin having a molecular weight of 2,000 or smaller, polyethylene glycol having a molecular weight of 10,000 or smaller, and polypropylene glycol having a molecular weight of 1,000 or smaller. Of them, diglycerin, polyethylene glycol 200, polyethylene glycol 400, polyethylene glycol 1000, polyethylene glycol 1540, dipropylene glycol, polypropylene glycol (3), and polypropylene glycol (7) are preferred from the viewpoint of a moist feeling of the skin after rinsing or after wiping.

Examples of the glyceryl ethers having an alkylene group added to glycerin include polyoxypropylene diglyceryl ether, polyoxypropylene glyceryl ether, and polyoxybutylene polyoxyethylene polyoxypropylene glyceryl ether. Of them, polyoxypropylene (9) diglyceryl ether, polyoxypropylene (14) diglyceryl ether, or polyoxybutylene polyoxyethylene polyoxypropylene glyceryl ether (3B.O.)(8E.O.)(5P.O.) is preferred from the viewpoint of low stickiness.

Examples of the sugars include sorbitol, erythritol, pentaerythritol, methyl glucoside, ethyl glucoside, polyoxyethylene methyl glucoside, and polyoxypropylene methyl glucoside. Alkyl glucoside having 2 or less of carbon atom in the alkyl chain is preferred. Of them, methyl glucoside, ethyl glucoside, polyoxyethylene methyl glucoside, or polyoxypropylene methyl glucoside is preferred. Polyoxyethylene methyl glucoside and polyoxypropylene methyl glucoside are more preferred from the viewpoint of a moist feeling of the skin after rinsing or after wiping.

The water-soluble solvent as the component (K) can be used alone or in combination of two or more thereof. The content of the water-soluble solvent in the total composition is preferably 1 mass % or more, more preferably 3 mass % or more, further more preferably 5 mass % or more, and is preferably 35 mass % or less, more preferably 20 mass % or less, further more preferably 15 mass % or less, from the viewpoint of offering a moist feeling and low stickiness. The content of the water-soluble solvent having an IOB of 0.5 to 6 in the total composition is preferably from 1 to 35 mass %, more preferably from 3 to 20 mass %, further more preferably from 5 to 15 mass %.

The O/W emulsion can further comprise (L) a nonionic surfactant having an HLB of 8 or more.

The HLB refers to an index which indicates a hydrophile-lipophile balance. In the present invention, a value calculated using the following expression of Oda, Teramura, etc. is used:

$$HLB\ value = \frac{\Sigma\ \text{Inorganic value}}{\Sigma\ \text{Organic value}} \times 10$$

The nonionic surfactant having an HLB of 8 or more as the component (L) preferably has an HLB of from 8 to 15. Examples thereof include polyglycerin fatty acid ester, polyethylene glycol fatty acid ester, polyoxyethylene glycerin fatty acid ester, polyoxyethylene polyoxypropylene glycol, polyoxyethylene sorbitan fatty acid ester, polyoxyethylene sorbitol fatty acid ester, polyoxyethylene castor oil, polyoxyethylene hydrogenated castor oil, polyoxyethylene hydrogenated castor oil fatty acid ester, polyoxyethylene alkyl ether, polyoxyethylene alkyl ether fatty acid ester, sucrose fatty acid ester, alkyl polyglucoside, and (poly)alkyl glyceryl ether.

Of them, polyglycerin fatty acid ester, polyethylene glycol fatty acid ester, polyoxyethylene glycerin fatty acid ester, polyoxyethylene sorbitan fatty acid ester, polyoxyethylene hydrogenated castor oil fatty acid ester, alkyl polyglucoside, and (poly)alkyl glyceryl ether are preferred from the viewpoint of a cleansing power. Polyethylene glycol fatty acid ester is preferred, and polyethylene glycol (12) monolaurate is more preferred, from the viewpoint of stability.

The nonionic surfactant having an HLB of 8 or more as the component (L) can be used alone or in combination of two or more thereof. The content of the nonionic surfactant having an HLB of 8 or more in the total composition is preferably 0.001 mass % or more, more preferably 0.01 mass % or more, further more preferably 0.03 mass % or more, and is preferably 5 mass % or less, more preferably 1 mass % or less, further more preferably 0.5 mass % or less, from the viewpoint of a cleansing power and low stickiness. The content of the nonionic surfactant having an HLB of 8 or more as the component (L) in the total composition is preferably from 0.001 to 5 mass %, more preferably from 0.01 to 1 mass %, further more preferably from 0.03 to 0.5 mass %.

The O/W emulsion can comprise (M) water which balances the components. The content of the water in the total composition is preferably 30 mass % or more, more preferably 40 mass % or more, further more preferably 50 mass % or more, and is preferably 95 mass % or less, more preferably 90 mass % or less, further more preferably 80 mass % or less.

The O/W emulsion can comprise, in addition to the components described above, a component used in ordinary cleansing compositions, for example, an oil agent other than the components (H) and (I), a polymer other than the component (J), an anionic surfactant, a cationic surfactant, an amphoteric surfactant, a bactericide, an anti-inflammatory agent, an antiseptic, a chelating agent, a salt, a pearling agent, a fragrance, a cooling agent, a dye, an ultraviolet absorber, an antioxidant, and a plant extract.

Examples of the oil agent other than the components (H) and (I) include hydrocarbon oils, such as liquid paraffin, having a viscosity exceeding 30 mPa·s at 30° C. The oil agent other than the components (H) and (I) can be used alone or in combination of two or more thereof. The content of the oil agent other than the components (H) and (I) in the total composition is preferably 0.01 mass % or more, and is preferably 50 mass % or less, more preferably 40 mass % or less, further more preferably 30 mass % or less, still further more preferably 20 mass % or less.

Examples of the polymer other than the component (J) include sodium hyaluronate.

The O/W emulsion can be produced according to a conventional method by mixing the components to be contained. The skin cleansing composition comprising a starting material which is solid at normal temperature can be produced by thermally melting the solid material or dissolving the solid material in other components and then uniformly mixing all components.

In the skin cleansing sheet of the present invention, the nonwoven as described above is impregnated with the O/W emulsion. Examples of methods for impregnating the nonwoven with the O/W emulsion include a method of applying the O/W emulsion to the nonwoven by dropwise addition or falling from a nozzle, and a method of impregnating the nonwoven with the O/W emulsion by spraying.

The rate of impregnation of the nonwoven with the O/W emulsion is preferably from 50 to 1,500%, more preferably from 300 to 700%, from the viewpoint of a cleansing power, comfortability for wiping, a fresh feeling, and usability. The rate of impregnation is calculated according to the following expression:

Rate of impregnation (%)=((Weight of the nonwoven impregnated with the impregnating solution)/(Weight of the dried nonwoven)−1)×100

The thickness of the sheet after the impregnation with the O/W emulsion is preferably from 100 to 2,000 μm, more preferably from 250 to 800 μm.

The skin cleansing sheet of the present invention is suitable as, for example, a facial wash or a cleansing agent and is more preferably a cleansing agent. Also, the skin cleansing sheet of the present invention is preferably used for cleansing a makeup cosmetic applied on the face.

The amount of the solution per unit volume in the second layers is preferably from $1\times10^6$ to $3\times10^6$ g/m$^3$, more preferably from $1.02\times10^6$ to $2.8\times10^6$ g/m$^3$, further more preferably from $1.04\times10^6$ to $2.6\times10^6$ g/m$^3$, from the viewpoint of a feeling that a large amount of the solution is contained in the sheet upon wiping, the gentleness in wiping the skin, and improved stability.

The amount of the solution per unit volume in the second layers is calculated according to the following expression:

$$\text{Amount of the solution per unit volume in the second layers (g/m}^3) = \frac{P \times Q \times 0.01}{R}$$

P: basis weight (g/m$^2$)
Q: the rate of impregnation (%)
R: the thickness of the second layers (m)

The skin cleansing sheet of the present invention can stably maintain its quality when laminated, after the impregnation with the O/W emulsion. The skin cleansing sheet of the present invention can also stably maintain its quality when the folded sheet is preserved.

In the skin cleansing sheet of the present invention, as mentioned above, the first layer having a high density is disposed as an intermediate layer in the thickness direction of the sheet, and the second layers having a low density are disposed on both surfaces thereof. The sheet is folded such that either surface forms the upper and lower inner surfaces facing each other (FIG. 1).

In the folded sheet, the oozing (movement) of the impregnating solution exhibits different behaviors between the inner surface side and the outer surface side of the folded sheet. In the outer surface of the sheet, as mentioned above, the oozing (movement) of the solution is prevented by the effects of the first layer. As a result, the quality is stably maintained. In contrast, the upper and lower inner surfaces of the folded sheet are come in contact with each other so that the impregnating solution more easily oozes (moves) as the second layer is more deformed (collapsed in the thickness direction) due to the self weight. In the sheet of the present invention, the nonwoven has moderate elasticity by virtue of the first layer having a high density. The sheet therefore deflects at the folded site to suppress the deformation attributed to the contact between the inner surfaces of the second layer.

Thus, since the oozing of the solution from the outer surface side to the inner surface side and between the inner surfaces is prevented by the first layer, the movement of the impregnating solution is predominantly movement in the planar direction of the sheet. In the sheet of the present invention, a folding site is formed, and this folding site prevents the movement of the solution in the planar direction. Specifically, the second layer having a lower density than that of the first layer tends to be deformed in the thickness direction. The density of the inside of the folding site in the folded sheet increases and is larger than the density of the facing surfaces of the second layer and close to, albeit smaller than, the density of the first layer. This can prevent the movement of the solution on the inner surface side similarly to the effects of the first layer. The density of the inside of the folding site in the second layer is preferably from 0.05 to 0.28 g/cm$^3$, more preferably from 0.07 to 0.19 g/cm$^3$, further more preferably from 0.09 to 0.17 g/cm$^3$.

In contrast, in the outer surface, the folding site is not deformed at a sharp angle due to the influence of the first layer having a high density and is instead deformed to deflect outward. The second layer is elongated as compared with the deformation at a sharp angle so that the fibers are partially decreased. In this case, the sparse structure is rendered sparser, and the thickness also decreases. This prevents the movement of the impregnating solution in the planar direction in the outer surface. The density of the outside of the folding site in the second layer is preferably from 0.005 to 0.26 g/cm$^3$, more preferably from 0.01 to 0.17 g/cm$^3$, further more preferably from 0.02 to 0.15 g/cm$^3$.

As mentioned above, the density of the second layer in the inner surfaces of the folding site is increased. In light of the layered structure of the fibers, the movement of the solution in the planar direction of the second layer tends to occur due to oozing from the second layer to the first layer, resulting in relative difference in the amount of the impregnating solution retained between the upper inner surface and the lower inner surface of the folded sheet. As a result, the solution easily moves from the lower inner surface to the upper inner surface by the capillary action brought about by the structure. The ratio of the density of the inside of the folding site to the density of the facing surfaces of the second layer, (the density of the inside of the folding site/the density of the facing surfaces), in the folded sheet is larger than 1, preferably 1.01 or more, more preferably 1.03 or more, further more preferably 1.05 or more, and is preferably 3.5 or less, more preferably 2.0 or less, further more preferably 1.8 or less, still further more preferably 1.5 or less.

In relation to the embodiments mentioned above, the present invention further discloses the following compositions:

<1> A skin cleansing composition comprising the following components (A), (B), (C), (D), and (E):
(A) 0.1 to 25 mass % of an ether oil which is in a liquid state at 25° C.,
(B) 0.003 to 1 mass % of a water-soluble polymer comprising acrylic acid or methacrylic acid as a constitutional unit,
(C) 1 to 30 mass % of a hydrocarbon oil having a viscosity of 15 mPa·s or lower at 30° C.,
(D) 60 to 95 mass % of water, and
(E) 0.49 mass % or less of a nonionic surfactant having an HLB of larger than 9, wherein
the mass ratio of the component (B) to the component (A), (B)/(A) is from 0.0001 to 0.1, and the mass ratio between the component (A) and the component (C), (A)/((A)+(C)) is from 0.05 to 0.9.

<2> The skin cleansing composition according to <1>, wherein the component (A) is preferably a dialkyl ether having two alkyl groups each having 16 or less of carbon atom, more preferably a dialkyl ether having two alkyl groups each having 8 or less of carbon atom.

<3> The skin cleansing composition according to <1> or <2>, wherein the component (A) is preferably octyl ether, cetyl-1,3-dimethyl butyl ether, dicaprylyl ether, dihexyl ether, or dilauryl ether, more preferably cetyl-1,3-dimethyl butyl ether or dioctyl ether, further more preferably dioctyl ether.

<4> The skin cleansing composition according to any one of <1> to <3>, wherein the content of the component (A) in the total composition is preferably 0.5 mass % or more, more preferably 1 mass % or more, and is preferably 10 mass % or less, more preferably 6 mass % or less, and the content of the component (A) in the total composition is preferably from 0.5 to 10 mass %, more preferably from 1 to 6 mass %.

<5> The skin cleansing composition according to any one of <1> to <4>, wherein the component (B) is preferably a carboxyvinyl polymer or an acrylic acid/alkyl methacrylate copolymer, more preferably an acrylic acid/alkyl methacrylate copolymer.

<6> The skin cleansing composition according to any one of <1> to <5>, wherein the content of the component (B) in the total composition is preferably 0.01 mass % or more, more preferably 0.05 mass % or more, and is preferably 0.5 mass % or less, more preferably 0.1 mass % or less, and the content of the component (B) in the total composition is preferably from 0.01 to 0.5 mass %, more preferably from 0.05 to 0.1 mass %.

<7> The skin cleansing composition according to any one of <1> to <6>, wherein the mass ratio of the component (B) to the component (A), (B)/(A) is preferably 0.0001 or more, more preferably 0.001 or more, further more preferably 0.01 or more, and is preferably 0.1 or less, more preferably 0.085 or less, further more preferably 0.07 or less, and the mass ratio of the component (B) to the component (A), (B)/(A) is preferably from 0.0001 to 0.1, more preferably from 0.001 to 0.085, further more preferably from 0.01 to 0.07.

<8> The skin cleansing composition according to any one of <1> to <7>, wherein the hydrocarbon oil as the component (C) has a viscosity of preferably 15 mPa·s or lower, more preferably from 1 to 10 mPa·s, at 30° C.

<9> The skin cleansing composition according to any one of <1> to <8>, wherein the content of the component (C) in the total composition is preferably 5 mass % or more, more preferably 8 mass % or more, and is preferably 25 mass % or less, more preferably 15 mass % or less, and the content of the component (C) in the total composition is preferably from 5 to 25 mass %, more preferably from 8 to 15 mass %.

<10> The skin cleansing composition according to any one of <1> to <9>, wherein the mass ratio between the component (A) and the component (C), (A)/((A)+(C)) is preferably 0.08 or more, more preferably 0.1 or more, and is preferably 0.8 or less, more preferably 0.4 or less, and the mass ratio between the component (A) and the component (C), (A)/((A)+(C)) is preferably from 0.08 to 0.8, more preferably from 0.1 to 0.4.

<11> The skin cleansing composition according to any one of <1> to <10>, wherein the content of the component (D) in the total composition is preferably 65 mass % or more, more preferably 70 mass % or more, and is preferably 90 mass % or less, more preferably 85 mass % or less, and the content of the component (D) in the total composition is preferably from 65 to 90 mass %, more preferably from 70 to 85 mass %.

<12> The skin cleansing composition according to any one of <1> to <11>, wherein the mass ratio of the component (A) to the component (D), (A)/(D) is preferably 0.001 or more, more preferably 0.01 or more, further more preferably 0.02 or more, and is preferably 0.45 or less, more preferably 0.25 or less, further more preferably 0.15 or less, and the mass ratio of the component (A) to the component (D), (A)/(D) is preferably from 0.001 to 0.45, more preferably from 0.01 to 0.25, further more preferably from 0.02 to 0.15.

<13> The skin cleansing composition according to any one of <1> to <12>, wherein the content of the nonionic surfactant in the total composition is preferably 0.0001 mass % or more, more preferably 0.005 mass % or more, further more preferably 0.01 mass % or more, and is preferably 0.049 mass % or less, and the content of the nonionic surfactant in the total composition is preferably from 0.0001 to 0.49 mass %, more preferably from 0.005 to 0.49 mass %, further more preferably from 0.01 to 0.049 mass %.

<14> The skin cleansing composition according to any one of <1> to <13>, wherein the component (E) is preferably polyglycerin fatty acid ester, polyethylene glycol fatty acid ester, polyoxyethylene glycerin fatty acid ester, propylene glycol fatty acid ester, polyoxyethylene polyoxypropylene glycol, sorbitan fatty acid ester, polyoxyethylene sorbitan fatty acid ester, polyoxyethylene sorbitol fatty acid ester, polyoxyethylene castor oil, polyoxyethylene hydrogenated castor oil, polyoxyethylene hydrogenated castor oil fatty acid ester, polyoxypropylene polyglyceryl ether, polyalkyl glyceryl ether, polyoxyethylene alkyl ether, polyoxyethylene alkyl ether fatty acid ester, sucrose fatty acid ester, alkyl polyglucoside, or (poly)alkyl glyceryl ether, more preferably polyglycerin fatty acid ester, polyethylene glycol fatty acid ester, polyoxyethylene glycerin fatty acid ester, polyoxyethylene sorbitan fatty acid ester, alkyl polyglucoside, or (poly)alkyl glyceryl ether.

<15> The skin cleansing composition according to any one of <1> to <14>, wherein the content of the component (E) in the total composition is preferably 0.0001 mass % or more, more preferably 0.005 mass % or more, further more preferably 0.01 mass % or more, and is preferably 3 mass % or less, more preferably 0.49 mass % or less, further more preferably 0.049 mass % or less, and the content of the nonionic surfactant in the total composition is preferably from 0.0001 to 3 mass %, more preferably from 0.005 to 0.49 mass %, further more preferably from 0.01 to 0.049 mass %.

<16> The skin cleansing composition according to any one of <1> to <15>, wherein the mass ratio of the component (A) to the component (E), (A)/(E) is preferably 0.1 or more, more preferably 1 or more, further more preferably 40 or more, and is preferably 200,000 or less, more preferably 600 or less, further more preferably 200 or less, and the mass ratio of the component (A) to the component (E), (A)/(E) is preferably from 0.1 to 200,000, more preferably 1 to 600, further more preferably from 40 to 200.

<17> The skin cleansing composition according to any one of <1> to <16>, further comprising (F) a water-soluble solvent.

<18> The skin cleansing composition according to <17>, wherein the component (F) is preferably 1,3-butylene glycol, propylene glycol, isoprene glycol, glycerin, diglycerin, polyethylene glycol 200, polyethylene glycol 400, polyethylene glycol 1000, polyethylene glycol 1540, dipropylene glycol, polypropylene glycol (3), polypropylene glycol (7), polyoxypropylene (9) diglyceryl ether, polyoxypropylene (14) diglyceryl ether, polyoxybutylene polyoxyethylene polyoxypropylene glyceryl ether (3B.O.)(8E.O.)(5P.O.), polyoxyethylene methyl glucoside, or polyoxypropylene methyl glucoside.

<19> The skin cleansing composition according to <17> or <18>, wherein the content of the component (F) in the total composition is preferably 1 mass % or more, more preferably 3 mass % or more, further more preferably 5 mass % or more, and is preferably 35 mass % or less, more preferably 25 mass % or less, further more preferably 15 mass % or less, and the content of the component (F) in the total composition is preferably from 1 to 35 mass %, more preferably from 3 to 25 mass %, further more preferably from 5 to 15 mass %.

<20> The skin cleansing composition according to any one of <1> to <19>, wherein a sheet is preferably impregnated with the skin cleansing composition.

<21> A skin cleansing sheet which is preferably used in the form of a sheet impregnated with a skin cleansing composition according to any one of <1> to <20>.

<22> The skin cleansing sheet according to <21>, wherein the sheet is preferably a nonwoven, more preferably made of fibers having a cellulose content of 30 mass % or more, and the density is preferably from 0.05 to 0.3 g/cm$^3$, more preferably from 0.075 to 0.25 g/cm$^3$.

<23> The skin cleansing sheet according to <22>, wherein the average basis weight (mass per unit area) of the nonwoven of the sheet is preferably 40 g/m$^2$ or larger and preferably 100 g/m$^2$ or smaller, and is more preferably from 50 to 80 g/m$^2$.

<24> The skin cleansing sheet according to <22> or <23>, wherein the nonwoven of the sheet is preferably a sheet material in which two or more nonwovens are layered or laminated, more preferably one having a three-layer structure.

<25> The skin cleansing sheet according to any one of <22> to <24>, wherein the rate of impregnation of the nonwoven with the skin cleansing composition is preferably from 50 to 1,500%, more preferably from 300 to 700%.

<26> The skin cleansing composition according to any one of <1> to <25>, wherein the content of an oil agent other than the components (A) and (C) in the total composition is preferably 0.01 mass % or more, and is preferably 20 mass % or less, more preferably 10 mass % or less, further more preferably 5 mass % or less, still further more preferably 1 mass % or less.

<27> The skin cleansing composition according to any one of <1> to <26>, wherein the skin cleansing composition preferably contains neither a cationic surfactant nor an amphoteric surfactant.

<28> The skin cleansing composition according to any one of <1> to <27>, wherein the skin cleansing composition is suitably used in one selected from the group consisting of a facial wash and a cleansing agent, more preferably a cleansing agent, and is preferably used for cleansing a makeup cosmetic applied on the face.

<29> The skin cleansing composition according to any one of <1> to <27>, wherein the composition is preferably used, either directly or after being shaken up until uniform upon separation, by, for example, a method of impregnating a sheet with the composition and wiping the face with the sheet, a method of putting the composition on the palm of a hand, spreading it over the face, and then wiping it off with a sheet, a method of putting the composition on the palm of a hand, spreading it over the face, and then washing it off, a method of impregnating a sheet with the composition, spreading it over the face, and then washing it off, or a method of wiping the face by any of these methods and then washing off the composition.

<30> The skin cleansing composition according to any one of <1> to <27>, wherein the skin cleansing composition is further more preferably in the form of a sheet impregnated therewith.

<31> The skin cleansing composition according to <30>, wherein the sheet preferably comprises cotton.

<32> Use of a skin cleansing composition according to any one of <1> to <27> for the production of a cleansing agent for cleansing a makeup cosmetic applied on the face.

<33> Use of a skin cleansing composition according to any one of <1> to <27> for the production of a cleansing agent for cleansing a makeup cosmetic applied on the face, wherein the cleansing agent is used such that a sheet is impregnated with the cleansing agent and the face is wiped with the sheet.

<34> Use of a skin cleansing composition according to any one of <1> to <27> for the production of a cleansing agent for cleansing a makeup cosmetic applied on the face, wherein the cleansing agent is used in the form of a sheet impregnated therewith.

<35> A skin cleansing composition comprising the following components (A), (B), (C), (D), and (E):
(A) 0.1 to 25 mass % of an ether oil which is in a liquid state at 25° C.,
(B) 0.003 to 1 mass % of a water-soluble polymer comprising acrylic acid or methacrylic acid as a constitutional unit,
(C) 1 to 30 mass % of a hydrocarbon oil having a viscosity of 15 mPa·s or lower at 30° C.,
(D) 60 to 95 mass % of water, and
(E) 0.49 mass % or less of a nonionic surfactant having an HLB larger than 9, wherein
the mass ratio between the component (A) and the component (C), (A)/((A)+(C)) is from 0.05 to 0.9, and the mass ratio of the component (A) to the component (E), (A)/(E), is from 40 to 200.

<36> A skin cleansing sheet comprising a nonwoven having a layered structure comprising a first layer and two second layers respectively disposed on surfaces of the first layer, and an O/W emulsion having a viscosity of from 200 to 15,000 mPa·s at 30° C. as an impregnating solution, wherein the ratio of the density of the first layer to the density of the second layers, (the density of the first layer/the density of the second layers), in the nonwoven is 1.05 or more, and the ratio of the thickness of the first layer to the thickness of one of the second layers, (the thickness of the first layer/the thickness of one of the second layers), in the nonwoven is from 0.6 to 1.5.

<37> The skin cleansing sheet according to <36>, wherein the ratio of the density of the first layer to the density of the second layers, (the density of the first layer/the density of the second layers) in the nonwoven is preferably 1.1 or more, more preferably 1.15 or more, and is preferably 2.3 or less, more preferably 2.0 or less, further more preferably 1.7 or less.

<38> The skin cleansing sheet according to <36> or <37>, wherein the porosity of pulp is preferably from 0.01 to 0.2, more preferably from 0.02 to 0.1, and the porosity of cotton is preferably from 0.001 to 0.04, more preferably from 0.002 to 0.02.

<39> The skin cleansing sheet according to any one of <36> to <38>, wherein the density of the first layer (intermediate layer) in the nonwoven is preferably 0.08 g/cm$^3$ or larger, more preferably 0.1 g/cm$^3$ or larger, further more preferably 0.12 g/cm$^3$ or larger, and is preferably 0.3 g/cm$^3$ or smaller, more preferably 0.2 g/cm$^3$ or smaller, further more preferably 0.18 g/cm$^3$ or smaller.

<40> The skin cleansing sheet according to any one of <36> to <39>, wherein the density of the second layers (surface layers) in the nonwoven is preferably 0.04 g/cm$^3$ or larger, more preferably 0.06 g/cm$^3$ or larger, further more preferably 0.08 g/cm$^3$ or larger, and is preferably 0.27 g/cm$^3$ or smaller, more preferably 0.18 g/cm$^3$ or smaller, further more preferably 0.16 g/cm$^3$ or smaller.

<41> The skin cleansing sheet according to any one of <36> to <40>, wherein the first layer in the nonwoven is preferably selected from the group consisting of hydrophilic fibers of cellulose such as pulp, cotton, rayon, cupra, and lyocell.

<42> The skin cleansing sheet according to any one of <36> to <41>, wherein the fiber thickness of the first layer in the nonwoven is preferably from 5 to 100 μm, more preferably from 10 to 40 μm.

<43> The skin cleansing sheet according to any one of <36> to <42>, wherein the basis weight of the first layer in the nonwoven is preferably from 10 to 80 g/m$^2$, more preferably from 15 to 30 g/m$^2$.

<44> The skin cleansing sheet according to any one of <36> to <43>, wherein the thickness of the first layer in the nonwoven is preferably from 50 to 700 μm, more preferably from 100 to 300 μm.

<45> The skin cleansing sheet according to any one of <36> to <44>, wherein the second layers in the nonwoven are preferably selected from the group consisting of cotton, rayon, lyocell, PET, and nylon.

<46> The skin cleansing sheet according to any one of <36> to <45>, wherein the fiber thickness of the second layers in the nonwoven is preferably from 1 to 80 μm, more preferably from 10 to 30 μm.

<47> The skin cleansing sheet according to any one of <36> to <46>, wherein the basis weight of the second layers in the nonwoven is preferably from 10 to 80 g/m$^2$, more preferably from 10 to 40 g/m$^2$, in total of the two second layers.

<48> The skin cleansing sheet according to any one of <36> to <47>, wherein the thickness of each of the second layers in the nonwoven is preferably from 50 to 500 μm, more preferably from 100 to 300 μm.

<49> The skin cleansing sheet according to any one of <36> to <47>, wherein the ratio of the thickness of the first layer to the thickness of one of the second layers, (the thickness of the first layer/the thickness of one of the second layers) in the nonwoven is preferably from 0.2 to 5.0, more preferably from 0.4 to 2.5, further more preferably from 0.5 to 2.0, still further more preferably from 0.6 to 1.5.

<50> The skin cleansing sheet according to any one of <36> to <49>, wherein the average fiber diameter of the fibers constituting the nonwoven is preferably from 1 to 50 μm, more preferably from 5 to 30 μm.

<51> The skin cleansing sheet according to any one of <36> to <50>, wherein in the nonwoven, a mixed layer of the fibers of the first layer and each of the second layers is preferably formed in more boundaries between the first layer and the second layers formed through complexation by a hydroentangling method, and the mixed layer of the fibers is more preferably formed between the first layer and each of the second layers such that the thickness of the mixed layer on one side accounts for from 5 to 40%, further more preferably from 10 to 35%, of the total thickness of the sheet comprising the first layer and the two second layers.

<52> The skin cleansing sheet according to any one of <36> to <51>, wherein a relief structure is preferably imparted to both surfaces of the sheet.

<53> The skin cleansing sheet according to any one of <36> to <52>, wherein the total basis weight of the nonwoven is preferably from 20 to 150 g/m$^2$, more preferably from 35 to 80 g/m$^2$.

<54> The skin cleansing sheet according to any one of <36> to <53>, wherein the ratio of the basis weight of the first layer to the basis weight of one of the second layers, (the basis weight of the first layer/the basis weight of one of the second layers) in the nonwoven is preferably from 0.2 to 5.0, more preferably from 0.4 to 2.0.

<55> The skin cleansing sheet according to any one of <36> to <54>, wherein the thickness of the nonwoven is preferably from 0.1 to 1.5 mm, more preferably from 0.3 to 0.7 mm.

<56> The skin cleansing sheet according to any one of <36> to <55>, wherein the saturation water level in the nonwoven is preferably from 500 to 1,500%, more preferably from 750 to 1,000%.

<57> The skin cleansing sheet according to any one of <36> to <56>, wherein for the nonwoven, preferably, pulp is used as the first layer, and cotton is used as the second layers.

<58> The skin cleansing sheet according to any one of <36> to <57>, wherein the mass ratio of cotton to all fibers, cotton/(cotton+pulp), is preferably from 0.3 to 0.95, more preferably from 0.5 to 0.6.

<59> The skin cleansing sheet according to any one of <36> to <58>, wherein the O/W emulsion with which the nonwoven is impregnated preferably has a viscosity of from 500 to 3,000 mPa·s at 30° C.

<60> The skin cleansing sheet according to any one of <36> to <59>, wherein the O/W emulsion can comprise (H) an ether oil which is in a liquid state at 25° C., and the viscosity of the ether oil which is in a liquid state at 25° C. as the component (H) is preferably 50 mPa·s or lower, more preferably 15 mPa·s or lower.

<61> The skin cleansing sheet according to <60>, wherein the component (H) is preferably a dialkyl ether having two alkyl groups each having 16 or less of carbon atom, more preferably a dialkyl ether having two alkyl groups each having 8 or less of carbon atom.

<62> The skin cleansing sheet according to <60> or <61>, wherein the component (H) is preferably cetyl-1,3-dimethyl butyl ether or dioctyl ether, more preferably dioctyl ether.

<63> The skin cleansing sheet according to any one of <60> to <62>, wherein the content of the component (H) in the total composition is preferably 0.1 mass % or more, more preferably 0.5 mass % or more, further more preferably 1 mass % or more, and is preferably 25 mass % or less, more preferably 10 mass % or less, further more preferably 6 mass % or less.

<64> The skin cleansing sheet according to any one of <36> to <63>, wherein the O/W emulsion can comprise (I) a hydrocarbon oil having a viscosity of 30 mPa·s or lower, preferably from 1 to 10 mPa·s, at 30° C.

<65> The skin cleansing sheet according to <64>, wherein the component (I) is preferably isododecane.

<66> The skin cleansing sheet according to <64> or <65>, wherein the content of the component (I) in the total composition is preferably 1 mass % or more, more preferably 5 mass % or more, further more preferably 10 mass % or more, and is preferably 50 mass % or less, more preferably 35 mass % or less, further more preferably 20 mass % or less.

<67> The skin cleansing sheet according to any one of <36> to <66>, wherein the O/W emulsion can comprise (J) a water-soluble polymer.

<68> The skin cleansing sheet according to <67>, wherein the component (J) is preferably a nonionic water-soluble polymer comprising cellulose as a constitutional unit, more preferably a hydroxyalkylcellulose, further more preferably hydroxyethylcellulose.

<69> The skin cleansing sheet according to <67>, wherein the component (J) is preferably a water-soluble polymer comprising acrylic acid or methacrylic acid as a constitutional unit, more preferably an acrylic acid/alkyl methacrylate copolymer, further more preferably a copolymer of acrylic acid and alkyl methacrylate having 10 to 30 of carbon atom ((acrylic acid/alkyl acrylate (C10-30)) copolymer).

<70> The skin cleansing sheet according to any one of <67> to <69>, wherein the content of the component (J) in the total composition is preferably 0.01 mass % or more, more preferably 0.025 mass % or more, further more preferably 0.05 mass % or more, and is preferably 1 mass % or less, more preferably 0.7 mass % or less, further more preferably 0.3 mass % or less.

<71> The skin cleansing sheet according to any one of <67> to <70>, wherein the mass ratio of the component (J) to the component (H), (J)/(H) in the O/W emulsion is preferably 0.001 or more, more preferably 0.004 or more, further more preferably 0.01 or more, and is preferably 5 or less, more preferably 2.5 or less, further more preferably 1 or less.

<72> The skin cleansing sheet according to any one of <36> to <71>, wherein the O/W emulsion can comprise (K) a water-soluble solvent.

<73> The skin cleansing sheet according to <72>, wherein the component (K) is preferably propylene glycol, isoprene glycol, 1,3-butylene glycol, hexylene glycol, or glycerin, more preferably 1,3-butylene glycol, propylene glycol, isoprene glycol, or glycerin.

<74> The skin cleansing sheet according to <72>, wherein the component (K) is preferably polyoxypropylene (9) diglyceryl ether, polyoxypropylene (14) diglyceryl ether, or polyoxybutylene polyoxyethylene polyoxypropylene glyceryl ether (3B.O.)(8E.O.)(5P.O.).

<75> The skin cleansing sheet according to any one of <72> to <74>, wherein the content of the component (K) in the total composition is preferably 1 mass % or more, more preferably 3 mass % or more, further more preferably 5 mass % or more, is preferably 35 mass % or less, more preferably 20 mass % or less, further more preferably 15 mass % or less.

<76> The skin cleansing sheet according to any one of <36> to <75>, wherein the O/W emulsion can comprise (L) a nonionic surfactant having an HLB of 8 or more.

<77> The skin cleansing sheet according to <76>, wherein the component (L) is preferably polyethylene glycol fatty acid ester, more preferably polyethylene glycol (12) monolaurate.

<78> The skin cleansing sheet according to <76> or <77>, wherein the content of the component (L) in the total composition is preferably 0.001 mass % or more, more preferably 0.01 mass % or more, further more preferably 0.03 mass % or more, and is preferably 5 mass % or less, more preferably 1 mass % or less, further more preferably 0.5 mass % or less.

<79> The skin cleansing sheet according to any one of <36> to <78>, wherein the O/W emulsion can comprise (M) water, and the content of the water in the total composition is preferably 30 mass % or more, more preferably 40 mass % or more, further more preferably 50 mass % or more, and is preferably 95 mass % or less, more preferably 90 mass % or less, further more preferably 80 mass % or less.

<80> The skin cleansing sheet according to any one of <36> to <79>, wherein the rate of impregnation of the nonwoven with the O/W emulsion is preferably from 50 to 1,500%, more preferably from 300 to 700%.

<81> The skin cleansing sheet according to any one of <36> to <80>, wherein the amount of the solution per unit volume in the surface area of the second layers is preferably from $1 \times 10^6$ to $3 \times 10^6$ g/m$^3$, more preferably from $1.02 \times 10^6$ to $2.8 \times 10^6$ g/m$^3$, further more preferably from $1.04 \times 10^6$ to $2.6 \times 10^6$ g/m$^3$.

<82> Use of a skin cleansing sheet according to any one of <36> to <81> for the production of a skin cleansing sheet for cleansing a makeup cosmetic applied on the face.

EXAMPLES

Examples 1 to 7 and Comparative Examples 1 to 5

Each skin cleansing composition was produced according to the composition shown in Table 1 and evaluated for the shape of a membrane, the homogeneity of the membrane, the sustention of a moist feeling of the skin after wiping, the sustention of a soft and bouncy feeling of the skin after wiping, and the cleansing power against oil-based mascara. The results are also shown in Table 1.

(Production Method)

Weighed water as the component (D) was placed in a container, and the component (B) was added thereto with stirring using Disper (1,200 rpm, 10 min.) to prepare a solution. Then, the component (A), the component (C), and other components were added thereto, and the mixture was stirred using a homomixer to produce a skin cleansing composition. Its pH and viscosity were adjusted to from 5 to 7 and from 1,000 to 2,500 mPa·s, respectively. In Example 7, the skin cleansing composition of Example 1 was added dropwise at a predetermined rate of impregnation to a nonwoven and then left to stand for 1 day such that the composition was fully spread in the nonwoven to produce a skin cleansing sheet.

(Evaluation method)

(1) Shape of Membrane:

0.1 g of each liquid skin cleansing composition (Examples 1 to 6 and Comparative Examples 1 to 5) was added dropwise to a glass plate and wiped off with cotton, or a glass plate was wiped with the skin cleansing sheet (Example 7). Then, the glass plate was left to stand for 12 hours to form a membrane. Five expert panelists touched the membrane with their fingers and conducted evaluation according to five levels given below. The sum of the scores of the five panelists was used for determination.

5: Felt moist and soft and bouncy.
4: Felt slightly moist and soft and bouncy.
3: Neutral.
2: Hardly felt moist and soft and bouncy.
1: Not felt moist and soft and bouncy at all.

(2) Homogeneity of Membrane:

0.1 g of each liquid skin cleansing composition (Examples 1 to 6 and Comparative Examples 1 to 5) was added dropwise to a glass plate and wiped off with cotton, or a glass plate was wiped with the skin cleansing sheet (Example 7). Then, the glass plate was left to stand for 12 hours to form a membrane. Five expert panelists visually evaluated the form of the membrane according to five levels given below. The total of the scores of the five panelists was used for determination.

5: Very homogeneous appearance.
4: Almost homogeneous appearance.
3: Neutral.
2: Slightly inhomogeneous appearance.
1: Inhomogeneous appearance.

(3) Sustention of Moist Feeling of Skin after Wiping:

Five expert panelists massaged their foundation (Sofina Primavista Liquid Foundation Ocher 05; the same foundation was used in subsequent evaluations)-applied faces using 1 g of each liquid cleansing composition (Examples 1 to 6 and Comparative Examples 1 to 5) and wiped off the foundation with cotton, or wiped their foundation-applied faces with the skin cleansing sheet (Example 7). Then, the panelists kept quiet for 3 hours in a room of 20° C. and 40% RH and then evaluated a moist feeling of the skin according to five levels given below. The sum of the scores of the five panelists was used for determination.
5: Moist.
4: Slightly moist.
3: Neutral.
2: Hardly moist.
1: Not moist at all.
(4) Sustention of Soft and Bouncy Feeling of Skin after Wiping:

Five expert panelists massaged their foundation-applied faces using 1 g of each liquid cleansing composition (Examples 1 to 6 and Comparative Examples 1 to 5) and wiped off the foundation with cotton, or wiped their foundation-applied faces with the skin cleansing sheet (Example 7). Then, the panelists kept quiet for 3 hours in a room of 20° C. and 40% RH and then evaluated a soft and bouncy feeling of the skin according to five levels given below when touching their faces with the fingers. The sum of the scores of the five panelists was used for determination.
5: Felt soft and bouncy.
4: Felt slightly soft and bouncy.
3: Neutral.
2: Hardly felt soft and bouncy.
1: Not felt soft and bouncy at all.
(5) Cleansing Power Against Oil-based Mascara:

0.005 g of KOSE Sports Beauty Fasio Power Stay Mascara (Curl Long) BK001 (trade name) was uniformly applied as oil-based mascara (waterproof mascara) in a circular pattern of 1.2 cm in diameter onto slide glass and left to stand for 2 hours for drying. The oil-based mascara was lightly rubbed for 10 seconds by finger massage using approximately 0.05 g of each liquid cleansing composition (Examples 1 to 6 and Comparative Examples 1 to 5) and then wiped off with cotton, or the oil-based mascara is lightly rubbed for 10 seconds by finger massage using the skin cleansing sheet (Example 7) and thereby wiped off. Five panelists evaluated the removal of the mascara according to five levels given below. The sum of the scores of the five panelists was used for determination.
5: Approximately 5% or less of the amount of the mascara applied remained.
4: More than approximately 5% and 20% or less of the amount of the mascara applied remained.
3: More than approximately 20% and 50% or less of the amount of the mascara applied remained.
2: More than approximately 50% and 80% or less of the amount of the mascara applied remained.
1: More than approximately 80% of the amount of the mascara applied remained.

TABLE 1

| | Component (mass %) | Example 1 | 2 | 3 | 4 | 5 | 6 | 7 |
|---|---|---|---|---|---|---|---|---|
| A | Dioctyl ether*1 | 15 | 15 | 15 | 15 | 15 | 0 | 15 |
|   | Cetyl-1,3-dimethyl butyl ether*2 | 0 | 0 | 0 | 0 | 0 | 15 | 0 |
| B | Acrylic acid/alkyl methacrylate copolymer*5 | 1 | 0.5 | 0.1 | 0.05 | 0.01 | 0.05 | 1 |
| C | Isododecane*3 (3 mPa·s) | 5 | 5 | 5 | 5 | 5 | 5 | 5 |
|   | Decamethyl-cyclopentasiloxane*4 | 0 | 0 | 0 | 0 | 0 | 0 | 0 |
|   | Potassium hydroxide solution (48%)*6 | 0.43 | 0.22 | 0.043 | 0.022 | 0.0043 | 0.022 | 0.43 |
| D | Water | 78.57 | 79.28 | 79.857 | 79.928 | 79.9857 | 79.928 | 78.57 |
|   | Total | 100 | 100 | 100 | 100 | 100 | 100 | 100 |
|   | Total amount of water | 78.79 | 79.39 | 79.8793 | 79.939 | 79.9879 | 79.939 | 78.79 |
|   | A/(A + C) | 0.75 | 0.75 | 0.75 | 0.75 | 0.75 | 0.75 | 0.75 |
|   | A/D | 0.19 | 0.19 | 0.19 | 0.19 | 0.19 | 0.19 | 0.19 |
|   | B/A | 0.067 | 0.033 | 0.007 | 0.003 | 0.001 | 0.003 | 0.067 |
|   | B/D | 0.0127 | 0.0063 | 0.0013 | 0.0006 | 0.0001 | 0.0006 | 0.0127 |
|   | A/(A + D) | 0.75 | 0.75 | 0.75 | 0.75 | 0.75 | 0.75 | 0.75 |
|   | Nonwoven*7 | — | — | — | — | — | — | YES |
|   | Rate of impregnation | — | — | — | — | — | — | 500% |
|   | Shape of membrane | 21 | 22 | 24 | 24 | 21 | 21 | 24 |
|   | Homogeneity of membrane | 21 | 22 | 23 | 23 | 21 | 21 | 25 |
|   | Sustention of moist feeling of skin after wiping | 21 | 21 | 24 | 24 | 21 | 20 | 25 |
|   | Sustention of soft and bouncy feeling of skin after wiping | 20 | 20 | 23 | 22 | 20 | 20 | 24 |
|   | Cleansing power against oil-based mascara | 21 | 24 | 24 | 25 | 25 | 16 | 25 |

| | Component (mass %) | Comparative Example 1 | 2 | 3 | 4 | 5 |
|---|---|---|---|---|---|---|
| A | Dioctyl ether*1 | 15 | 15 | 20 | 0 | 0 |
|   | Cetyl-1,3-dimethyl butyl ether*2 | 0 | 0 | 0 | 0 | 0 |
| B | Acrylic acid/alkyl methacrylate copolymer*5 | 0.001 | 3 | 0.05 | 0.05 | 0.05 |

TABLE 1-continued

| | | | | | | |
|---|---|---|---|---|---|---|
| C | Isododecane*³ (3 mPa·s) | 5 | 5 | 0 | 20 | 0 |
| | Decamethylcyclopentasiloxane*⁴ | 0 | 0 | 0 | 0 | 20 |
| | Potassium hydroxide solution (48%)*⁶ | 0.00043 | 1.29 | 0.022 | 0.022 | 0.022 |
| D | Water | 79.99857 | 75.71 | 79.928 | 79.928 | 79.928 |
| | Total | 100 | 100 | 100 | 100 | 100 |
| | Total amount of water | 79.99879 | 76.38 | 79.939 | 79.939 | 79.939 |
| | A/(A + C) | 0.75 | 0.75 | 1 | 0 | — |
| | A/D | 0.19 | 0.20 | 0.25 | 0.00 | 0.00 |
| | B/A | 0.000067 | 0.2 | 0.2 | 0.003 | 0.003 |
| | B/D | 0.00001 | 0.0393 | 0.0006 | 0.0006 | 0.0006 |
| | A/(A + D) | 0.75 | 0.75 | 0.75 | — | — |
| | Nonwoven*⁷ | — | — | — | — | — |
| | Rate of impregnation | — | — | — | — | — |
| | Shape of membrane | 9 | 12 | 24 | 8 | 9 |
| | Homogeneity of membrane | 17 | 9 | 24 | 9 | 9 |
| | Sustention of moist feeling of skin after wiping | 15 | 15 | 24 | 9 | 10 |
| | Sustention of soft and bouncy feeling of skin after wiping | 15 | 15 | 15 | 8 | 9 |
| | Cleansing power against oil-based mascara | 24 | 15 | 24 | 17 | 5 |

*¹dioctyl ether: CETIOL OE (manufactured by BASF Japan Ltd.)
*²cetyl-1,3-dimethyl butyl ether: ASE-166K (manufactured by Kao Corp.)
*³isododecane: MARUKASOL R (manufactured by Maruzen Petrochemical Co., Ltd.), 3 mPa·s
*⁴SH245 (manufactured by Dow Corning Toray Co., Ltd.)
*⁵PEMULEN TR-2 (manufactured by Lubrizol Advanced Materials, Inc.)
*⁶liquid potassium hydroxide (48%): (manufactured by Asahi Glass Co., Ltd.)
*⁷CT-58MS (manufactured by Daiwabo Co., Ltd.; cotton: 55%, pulp: 45%, density: 0.13 g/cm³, basis weight: 58 g/m², thickness: 0.45 mm)

Examples 8 to 15 and Comparative Examples 6 to 14

Each skin cleansing composition was produced according to the composition shown in Tables 2 and 3, and its viscosity and average particle size were measured. The skin cleansing composition was evaluated for the sustention of a moist feeling of the skin after wiping, the sustention of a soft and bouncy feeling of the skin after wiping, and the cleansing power against oil-based mascara in the same way as in Examples 1 to 7 and also evaluated for the fresh feeling and moist feeling immediately after wiping, the feeling upon application after preservation, the thick feeling, the manageability, and the smoothness in wiping. The results are also shown in Tables 2 and 3.

(Production Method)

Weighed water as the component (D) was placed in a container, and the component (B) was added thereto with stirring using Disper (1,200 rpm, 10 min.) to prepare a solution. Then, the component (A), the component (C), and other components were added thereto, and the mixture was stirred using a homomixer to produce a skin cleansing composition. Its pH and viscosity were adjusted to fall within the ranges of 5 to 7 and 1,000 to 2,500 mPa·s, respectively. In Examples 9 to 15 and Comparative Examples 6 to 14, the skin cleansing composition was added dropwise at a predetermined rate of impregnation to a nonwoven and then left to stand for 1 day such that the composition was fully spread over the sheet to produce a skin cleansing sheet.

(Evaluation Method)

(1) Viscosity:

The viscosity of each skin cleansing composition before the impregnation of a sheet was measured at 25° C. using a B-type viscometer under conditions of rotor No. 2, 6 rpm, and 1 minute.

(2) Average Particle Size:

The particle sizes of emulsified particles of each skin cleansing composition before the impregnation of a sheet were measured using a laser diffraction/scattering particle size distribution analyzer (manufactured by HORIBA, Ltd., LA-910) after dilution with water into a concentration providing 70 to 95% transmittance to calculate an average particle size.

(3) Fresh Feeling Immediately after Wiping:

Five expert panelists massaged their foundation-applied faces using 1 g of the liquid cleansing composition (Example 8) and wiped off the foundation with cotton, or wiped their foundation-applied faces with each skin cleansing sheet (Examples 9 to 15 and Comparative Examples 6 to 14). Then, the panelists evaluated a fresh feeling according to five levels given below. The sum of the scores of the five panelists was used for determination.

5: Fresh.
4: Slightly fresh.
3: Neutral.
2: Not so fresh.
1: Not fresh at all.

(4) Moist Feeling Immediately after Wiping:

Five expert panelists massaged their foundation-applied faces using 1 g of the liquid cleansing composition (Example 8) and wiped off the foundation with cotton, or wiped their foundation-applied faces with each skin cleansing sheet (Examples 9 to 15 and Comparative Examples 6 to 14). Then, the panelists evaluated a moist feeling according to five levels given below. The sum of the scores of the five panelists was used for determination.

5: Moist.
4: Slightly moist.
3: Neutral.
2: Not so moist.
1: Not moist at all.

(5) Feeling Upon Application after Preservation:

The liquid cleansing composition (Example 8) charged in a 100-mL glass bottle (diameter: approximately 5 cm, height: approximately 8 cm, manufacturer: TGK Co., Ltd.) was preserved at 50° C. for 4 weeks. Then, approximately 1 g was gently sucked out of each of the upper portion (between the surface of the solution and 5 mm below) and lower portion (between the bottom and 5 mm above) of the composition using a dropping syringe (material: polyethylene, volume: 2 mL). Five expert panelists massaged their foundation-applied faces using the upper-portion and lower-portion samples of the liquid cleansing composition and wiped off the foundation with cotton, and then evaluated difference in a feeling upon application therebetween according to five levels given below. In addition, 40 pieces of each skin cleansing sheet (Examples 9 to 15 and Comparative Examples 6 to 14) were laminated, then sealed in an aluminum pillow, and preserved at 50° C. for 4 weeks. Then, five expert panelists compared use of the uppermost sheet and the lowermost sheet of the preserved laminate applied to their faces and evaluated difference in a feeling upon application therebetween according to five levels given below. The sum of the scores of the five panelists was used for determination.

5: Same.
4: Not so different.
3: Neutral.
2: Slightly different.
1: Different.

(6) Thick Feeling:

Five expert panelists massaged their foundation-applied faces using 1 g of the liquid cleansing composition (Example 8) and wiped off the foundation with cotton, or wiped their foundation-applied faces with each skin cleansing sheet (Examples 9 to 15 and Comparative Examples 6 to 14). Then, the panelists evaluated a thick feeling upon wiping according to five levels given below. The sum of the scores of the five panelists was used for determination.

The thick feeling represents the degree of deformation of the sheet upon wiping and means that the skin can be gently wiped in the presence of the thick feeling.

5: Thick feeling was perceived.
4: Thick feeling was slightly perceived.
3: Neutral.
2: Thick feeling was not perceived so much.
1: Thick feeling was not perceived.

(7) Manageability (No Dripping):

Five expert panelists massaged their foundation-applied faces using 1 g of the liquid cleansing composition (Example 8) and wiped off the foundation with cotton, or wiped their foundation-applied faces with each skin cleansing sheet (Examples 9 to 15 and Comparative Examples 6 to 14). Then, the panelists evaluated manageability upon wiping according to five levels given below. The sum of the scores of the five panelists was used for determination.

5: Manageable.
4: Slightly manageable.
3: Neutral.
2: Not so manageable.
1: Not manageable.

(8) Smoothness in Wiping:

Five expert panelists massaged their foundation-applied faces using 1 g of the liquid cleansing composition (Example 8) and wiped off the foundation with cotton, or wiped their foundation-applied faces with each skin cleansing sheet (Examples 9 to 15 and Comparative Examples 6 to 14). Then, the panelists evaluated smooth wiping according to five levels given below. The sum of the scores of the five panelists was used for determination.

5: Smooth.
4: Slightly smooth.
3: Neutral.
2: Not so smooth.
1: Not smooth at all.

TABLE 2

| | | Example | | | | | | | |
|---|---|---|---|---|---|---|---|---|---|
| | Component (mass %) | 8 | 9 | 10 | 11 | 12 | 13 | 14 | 15 |
| A | Dioctyl ether*[1] | 2 | 2 | 2 | 2 | 0 | 25 | 7 | 2 |
| | Alkyl-1,3-dimethyl butyl ether*[2] | 0 | 0 | 0 | 0 | 2 | 0 | 0 | 0 |
| B | Acrylic acid/alkyl methacrylate copolymer*[5] | 0.075 | 0.075 | 0.075 | 0.075 | 0.075 | 0.075 | 0.075 | 0.075 |
| C | Isododecane*[3] (3 mPa·s) | 12 | 10 | 10 | 10 | 12 | 5 | 12 | 12 |
| | Isohexadecane*[8] (5 mPa·s) | 0 | 1 | 1 | 1 | 0 | 0 | 0 | 0 |
| | Hydrogenated polyisobutene*[9] (14 mPa·s) | 0 | 1 | 1 | 1 | 0 | 0 | 0 | 0 |
| F | Polyoxypropylene (9) diglyceryl ether*[10] | 4 | 2 | 2 | 2 | 4 | 4 | 4 | 4 |
| | Polyoxybutylene polyoxyethylene polyoxypropylene glyceryl ether (3B.O.)(8E.O.)(5P.O.)*[11] | 0 | 1 | 1 | 1 | 0 | 0 | 0 | 0 |
| | 1,3-Butylene glycol*[12] | 5 | 2 | 2 | 2 | 5 | 5 | 5 | 5 |
| E | Polyethylene glycol (12) monolaurate*[13] (HLB = 14) | 0.045 | 0.045 | 0.045 | 0.045 | 0.045 | 0.045 | 0.045 | 0.045 |
| Others | Potassium hydroxide solution (48%)*[6] | 0.032 | 0.032 | 0.032 | 0.032 | 0.032 | 0.032 | 0.032 | 0.032 |
| | Methyl p-hydroxybenzoate*[14] | 0.1 | 0.1 | 0.1 | 0.1 | 0.1 | 0.1 | 0.1 | 0.1 |
| | Phenoxyethanol*[15] | 0.3 | 0.3 | 0.3 | 0.3 | 0.3 | 0.3 | 0.3 | 0.3 |
| D | Water | 76.448 | 80.448 | 80.448 | 80.448 | 76.448 | 60.448 | 71.448 | 76.448 |
| | Total | 100 | 100 | 100 | 100 | 100 | 100 | 100 | 100 |
| | Total amount of water | 76.465 | 80.465 | 80.465 | 80.465 | 76.465 | 60.465 | 71.465 | 76.465 |
| | Average particle size (μm) | 10 | 10 | 10 | 10 | 10 | 10 | 10 | 10 |
| | Viscosity (mPa·s) | 1200 | 1200 | 1200 | 1200 | 1200 | 2000 | 1600 | 1200 |
| | A/(A + C) | 0.14 | 0.14 | 0.14 | 0.14 | 0.14 | 0.83 | 0.37 | 0.14 |
| | B/A | 0.038 | 0.038 | 0.038 | 0.038 | 0.038 | 0.003 | 0.011 | 0.038 |
| | A/D | 0.026 | 0.025 | 0.025 | 0.025 | 0.026 | 0.414 | 0.098 | 0.026 |

TABLE 2-continued

| | Component (mass %) | Example 8 | 9 | 10 | 11 | 12 | 13 | 14 | 15 |
|---|---|---|---|---|---|---|---|---|---|
| A/E | | 44 | 44 | 44 | 44 | 44 | 556 | 156 | 44 |
| B/D | | 0.0010 | 0.0009 | 0.0009 | 0.0009 | 0.0010 | 0.0012 | 0.0010 | 0.0010 |
| A/F | | 0.222 | 0.400 | 0.400 | 0.400 | 0.222 | 2.778 | 0.778 | 0.222 |
| B/F | | 0.008 | 0.015 | 0.015 | 0.015 | 0.008 | 0.008 | 0.008 | 0.008 |
| (Support) | Single-layer structure nonwoven[16] | — | YES | — | — | — | — | — | — |
| | Single-layer combined-filament yarn structure nonwoven[17] | — | — | b | — | — | — | — | — |
| | Three-layer structure nonwoven[7] | — | — | — | b | b | b | b | b |
| | Basis weight (g/m$^2$) | — | 60 | 59 | 58 | 58 | 58 | 58 | 58 |
| | Average fiber diameter (μm) | — | 15 | 14 | 17 | 17 | 17 | 17 | 17 |
| | Thickness (μm) | — | 400 | 325 | 450 | 450 | 450 | 450 | 450 |
| Rate of impregnation (%) | | — | 400 | 400 | 500 | 500 | 500 | 500 | 500 |
| Evaluation | Sustention of moist feeling of skin after wiping | 21 | 20 | 20 | 23 | 24 | 21 | 23 | 25 |
| | Sustention of soft and bouncy feeling of skin after wiping | 21 | 22 | 22 | 22 | 23 | 21 | 23 | 25 |
| | Fresh feeling immediately after wiping | 25 | 23 | 23 | 23 | 23 | 16 | 20 | 25 |
| | Moist feeling immediately after wiping | 21 | 20 | 20 | 21 | 25 | 23 | 24 | 25 |
| | Feeling upon application after preservation | 21 | 24 | 24 | 24 | 24 | 16 | 22 | 25 |
| | Thick feeling | 20 | 22 | 20 | 25 | 25 | 25 | 25 | 25 |
| | Manageability (no dripping) | 16 | 25 | 25 | 25 | 25 | 25 | 25 | 25 |
| | Smoothness in wiping | 20 | 20 | 23 | 24 | 25 | 25 | 25 | 25 |
| | Cleansing power against oil-based mascara | 23 | 21 | 21 | 25 | 21 | 25 | 25 | 25 |

[1]dioctyl ether: CETIOL OE (manufactured by BASF Japan Ltd.)
[2]cetyl-1,3-dimethyl butyl ether: ASE-166K (manufactured by Kao Corp.)
[3]isododecane: MARUKASOL R (manufactured by Maruzen Petrochemical Co., Ltd.)
[5]PEMULEN TR-2 (manufactured by Lubrizol Advanced Materials, Inc.)
[8]isohexadecane: PARLEAM 4 (manufactured by NOF Corp.)
[9]hydrogenated polyisobutene: PARLEAM EX (manufactured by NOF Corp.)
[10]polyoxypropylene (9) diglyceryl ether: SY-DP9 (manufactured by Sakamoto Yakuhin Kogyo Co., Ltd.)
[11]polyoxybutylene polyoxyethylene polyoxypropylene glyceryl ether (3B.O.)(8E.O.)(5P.O.): WILBRIDE S-753 (manufactured by NOF Corp.)
[12]1,3-butylene glycol: 1,3-Butylene Glycol-P (manufactured by KH Neochem Co., Ltd.)
[13]polyethylene glycol (12) monolaurate: EMANON 1112 (manufactured by Kao Corp.)
[6]liquid potassium hydroxide (48%): (manufactured by Asahi Glass Co., Ltd.)
[14]methyl p-hydroxybenzoate: MEKKINSU M (manufactured by Ueno Fine Chemicals Industry, Ltd.)
[15]phenoxyethanol: NEOLONE PH 100 (manufactured by the Down Chemical Company)
[16]single-layer structure nonwoven: COTTOACE C060S/A01 (manufactured by Unitika Ltd.; cotton: 100%, density: 0.15 g/cm$^3$, basis weight: 60 g/m$^2$, thickness: 0.4 mm)
[17]single-layer combined-filament yarn structure nonwoven: COTTOACE C059L/A02 (manufactured by Unitika Ltd.; cotton: 70%, lyocell: 30%, density: 0.18 g/cm$^3$, basis weight 59 g/m$^2$, thickness: 0.33 mm)
[7]three-layer structure nonwoven: CT-58MS (manufactured by Daiwabo Co., Ltd.; cotton: 55%, pulp: 45%, density: 0.13 g/cm$^3$, basis weight: 58 g/m$^2$, thickness: 0.45 mm)

TABLE 3

| | Component (mass %) | Comparative Example 6 | 7 | 8 | 9 | 10 |
|---|---|---|---|---|---|---|
| A | Dioctyl ether[1] | 25 | 0.1 | 0 | 14 | 0 |
| | Alkyl-1,3-dimethyl butyl ether[2] | 0 | 0 | 0 | 0 | 0 |
| B | Acrylic acid/alkyl methacrylate copolymer[5] | 0.075 | 0.075 | 0.075 | 0 | 0.075 |
| C | Isododecane[3] (3 mPa · s) | 1 | 21 | 14 | 0 | 0 |
| | Isohexadecane[8] (5 mPa · s) | 0 | 0 | 0 | 0 | 0 |
| | Hydrogenated polyisobutene[9] (14 mPa · s) | 0 | 0 | 0 | 0 | 0 |
| F | Polyoxypropylene (9) diglyceryl ether[10] | 4 | 4 | 4 | 4 | 4 |
| | Polyoxybutylene polyoxyethylene polyoxypropylene glyceryl ether (3B.O.)(8E.O.)(5P.O.)[11] | 0 | 0 | 0 | 0 | 0 |
| | 1,3-Butylene glycol[12] | 5 | 5 | 5 | 5 | 5 |

TABLE 3-continued

|   |   |   |   |   |   |   |
|---|---|---|---|---|---|---|
| E | Polyethylene glycol (12) monolaurate*[13] (HLB = 14) | 0.045 | 0.045 | 0.045 | 0.045 | 0.045 |
| Others | Potassium hydroxide solution (48%)*[6] | 0.032 | 0.032 | 0.032 | 0 | 0.032 |
|   | Methyl p-hydroxybenzoate*[14] | 0.1 | 0.1 | 0.1 | 0.1 | 0.1 |
|   | Phenoxyethanol*[15] | 0.3 | 0.3 | 0.3 | 0.3 | 0.3 |
| D | Water | 64.448 | 69.348 | 76.448 | 76.555 | 90.448 |
| Total |   | 100 | 100 | 100 | 100 | 100 |
| Total amount of water |   | 64.465 | 69.365 | 76.465 | 76.555 | 90.465 |
| Average particle size (μm) |   | 10 | 10 | 10 | — | — |
| Viscosity (mPa · s) |   | 2000 | 1800 | 1200 | 10 or less | 900 |
| A/(A + C) |   | 0.96 | 0.005 | 0.00 | 1.00 | — |
| B/A |   | 0.003 | 0.750 | — | 0.0 | — |
| A/D |   | 0.388 | 0.001 | 0.000 | 0.183 | 0.000 |
| A/E |   | 556 | 2 | 0 | 311 | 0 |
| B/D |   | 0.0012 | 0.0011 | 0.0010 | 0.0000 | 0.0008 |
| A/F |   | 2.778 | 0.011 | 0 | 1.556 | 0 |
| B/F |   | 0.008 | 0.008 | 0.008 | 0 | 0.008 |
| Support | Single-layer structure non-woven*[16] | — | — | YES | YES | YES |
|   | Single-layer combined-filament yarn structure non-woven*[17] | — | — | — | — | — |
|   | Three-layer structure non-woven*[7] | b | b | — | — | — |
|   | Basis weight (g/m²) | 58 | 58 | 60 | 60 | 60 |
|   | Average fiber diameter (μm) | 17 | 17 | 15 | 15 | 15 |
|   | Thickness (μm) | 450 | 450 | 400 | 400 | 400 |
| Rate of impregnation (%) |   | 500 | 500 | 400 | 400 | 400 |
| Evaluation | Sustention of moist feeling of skin after wiping | 22 | 21 | 12 | 15 | 11 |
|   | Sustention of soft and bouncy feeling of skin after wiping | 19 | 9 | 12 | 15 | 12 |
|   | Fresh feeling immediately after wiping | 9 | 19 | 18 | 13 | 23 |
|   | Moist feeling immediately after wiping | 23 | 20 | 17 | 21 | 15 |
|   | Feeling upon application after preservation | 13 | 21 | 14 | 5 | 22 |
|   | Thick feeling | 25 | 25 | 22 | 8 | 19 |
|   | Manageability (no dripping) | 25 | 25 | 25 | 15 | 25 |
|   | Smoothness in wiping | 25 | 24 | 20 | 15 | 19 |
|   | Cleansing power against oil-based mascara | 25 | 22 | 19 | 24 | 5 |

| Component | | Comparative Example | | | |
|---|---|---|---|---|---|
| (mass %) | | 11 | 12 | 13 | 14 |
| A | Dioctyl ether*[1] | 38 | 0.05 | 2 | 35 |
|   | Alkyl-1,3-dimethyl butyl ether*[2] | 0 | 0 | 0 | 0 |
| B | Acrylic acid/alkyl methacrylate copolymer*[5] | 0.075 | 0.005 | 0.25 | 0.003 |
| C | Isododecane*[3] (3 mPa · s) | 12 | 12 | 12 | 12 |
|   | Isohexadecane*[8] (5 mPa · s) | 0 | 0 | 0 | 0 |
|   | Hydrogenated polyisobutene*[9] (14 mPa · s) | 0 | 0 | 0 | 0 |
| F | Polyoxypropylene (9) diglyceryl ether*[10] | 4 | 4 | 4 | 4 |
|   | Polyoxybutylene polyoxyethylene polyoxypropylene | 0 | 0 | 0 | 0 |

TABLE 3-continued

|   |   | | | | |
|---|---|---|---|---|---|
| | glyceryl ether (3B.O.)(8E.O.)(5P.O.)*11 | | | | |
| | 1,3-Butylene glycol*12 | 5 | 5 | 5 | 5 |
| E | Polyethylene glycol (12) monolaurate*13 (HLB = 14) | 0.045 | 0.045 | 0.045 | 0.045 |
| Others | Potassium hydroxide solution (48%)*6 | 0.032 | 0.002 | 0.11 | 0.001 |
| | Methyl p-hydroxy-benzoate*14 | 0.1 | 0.1 | 0.1 | 0.1 |
| | Phenoxyethanol*15 | 0.3 | 0.3 | 0.3 | 0.3 |
| D | Water | 40.448 | 78.498 | 76.195 | 43.551 |
| Total | | 100 | 100 | 100 | 100 |
| Total amount of water | | 40.465 | 78.499 | 76.252 | 43.552 |
| Average particle size (μm) | | 10 | 10 | 10 | 10 |
| Viscosity (mPa · s) | | 2200 | 10 or less | 4000 | 100 |
| A/(A + C) | | 0.76 | 0.004 | 0.14 | 0.74 |
| B/A | | 0.002 | 0.100 | 0.125 | 0.0001 |
| A/D | | 0.939 | 0.001 | 0.026 | 0.804 |
| A/E | | 844 | 1 | 44 | 778 |
| B/D | | 0.0019 | 0.0001 | 0.0033 | 0.0001 |
| A/F | | 4.222 | 0.006 | 0.222 | 3.889 |
| B/F | | 0.008 | 0.001 | 0.028 | 0.00033 |
| Support | Single-layer structure non-woven*16 | — | — | — | — |
| | Single-layer combined filament yarn structure non-woven*17 | — | — | — | — |
| | Three-layer structure non-woven*7 | b | b | b | b |
| | Basis weight (g/m²) | 58 | 58 | 58 | 58 |
| | Average fiber diameter (μm) | 17 | 17 | 17 | 17 |
| | Thickness (μm) | 450 | 450 | 450 | 450 |
| | Rate of impregnation (%) | 500 | 500 | 500 | 500 |
| Evaluation | Sustention of moist feeling of skin after wiping | 20 | 12 | 15 | 21 |
| | Sustention of soft and bouncy feeling of skin after wiping | 13 | 10 | 12 | 12 |
| | Fresh feeling immediately after wiping | 12 | 19 | 19 | 11 |
| | Moist feeling immediately after wiping | 23 | 19 | 19 | 22 |
| | Feeling upon application after preservation | 9 | 12 | 23 | 9 |
| | Thick feeling | 21 | 8 | 25 | 9 |
| | Manageability (no dripping) | 25 | 15 | 25 | 16 |
| | Smoothness in wiping | 24 | 17 | 25 | 18 |
| | Cleansing power against oil-based mascara | 25 | 19 | 9 | 25 |

*1 dioctyl ether: CETIOL OE (manufactured by BASF Japan Ltd.)
*2 cetyl-1,3-dimethyl butyl ether: ASE-166K (manufactured by Kao Corp.)
*3 isododecane: MARUKASOL R (manufactured by Maruzen Petrochemical Co., Ltd.)
*5 PEMULEN TR-2 (manufactured by Lubrizol Advanced Materials, Inc.)
*8 isohexadecane: PARLEAM 4 (manufactured by NOF Corp.)
*9 hydrogenated polyisobutene: PARLEAM EX (manufactured by NOF Corp.)
*10 polyoxypropylene (9) diglyceryl ether SY-DP9 (manufactured by Sakamoto Yakuhin Kogyo Co., Ltd.)
*11 polyoxybutylene polyoxyethylene polyoxypropylene glyceryl ether (3B.O.)(8E.O.)(5P.O.): WILBRIDE S-753 (manufactured by NOF Corp.)
*12 1,3-butylene glycol: 1,3-Butylene Glycol-P (manufactured by KH Neochem Co., Ltd.)
*13 polyethylene glycol (12) monolaurate: EMANON 1112 (manufactured by Kao Corp.)
*6 liquid potassium hydroxide (48%): (manufactured by Asahi Glass Co., Ltd.)
*14 methyl p-hydroxybenzoate: MEKKINSU M (manufactured by Ueno Fine Chemicals Industry, Ltd.)
*15 phenoxyethanol: NEOLONE PH 100 (manufactured by the Down Chemical Company)
*16 single-layer structure nonwoven: COTTOACE C060S/A01 (manufactured by Unitika Ltd.; cotton: 100%, density: 0.15 g/cm³, basis weight: 60 g/m², thickness: 0.4 mm)
*17 single-layer combined-filament yarn structure nonwoven: COTTOACE C059L/A02 (manufactured by Unitika Ltd.; cotton: 70%, lyocell: 30%, density: 0.18 g/cm³, basis weight: 59 g/m², thickness: 0.33 mm)
*7 three-layer structure nonwoven: CT-58MS (manufactured by Daiwabo Co., Ltd.; cotton: 55%, pulp: 45%, density: 0.13 g/cm³, basis weight 58 g/m², thickness: 0.45 mm)

Examples 15 to 17

In the same way as in Examples 8 to 15, each skin cleansing composition was produced according to the composition shown in Table 4, and its viscosity and average particle size were measured. The skin cleansing composition was evaluated for the sustention of a moist feeling of the skin after wiping, the sustention of a soft and bouncy feeling of the skin after wiping, the fresh feeling and moist feeling immediately after wiping, the feeling upon application after preservation, the thick feeling, the manageability, the smoothness in wiping, and the cleansing power against oil-based mascara and also evaluated for the absence of stickiness immediately after wiping. The results are also shown in Table 4.

(Evaluation Method)
(1) Absence of Stickiness Immediately after Wiping:

Five expert panelists massaged their foundation-applied faces using 1 g of each liquid cleansing composition and wiped off the foundation with cotton. Then, the panelists evaluated the absence of stickiness immediately after the wiping according to five levels given below. The sum of the scores of the five panelists was used for determination.

5: Stickiness was not perceived at all.
4: Stickiness was almost absent.
3: Neutral.
2: Stickiness was slightly perceived.
1: Stickiness was perceived.

TABLE 4

| | | | Example | | |
|---|---|---|---|---|---|
| | Component (mass %) | | 15 | 16 | 17 |
| A | Dioctyl ether*[1] | | 2 | 2 | 2 |
| B | Acrylic acid/alkyl methacrylate copolymer*[5] | | 0.075 | 0.075 | 0.075 |
| C | Isododecane*[3] (3 mPa · s) | | 12 | 12 | 12 |
| F | Polyoxypropylene (9) diglyceryl ether*[10] | | 4 | 4 | 4 |
| | 1,3-Butylene glycol*[12] | | 5 | 5 | 0 |
| | Glycerin | | 0 | 0 | 2 |
| | Sorbitol | | 0 | 0 | 3 |
| E | Polyethylene glycol (12) monolaurate*[13] (HLB = 14) | | 0.045 | 0.45 | 0.045 |
| Others | Potassium hydroxide solution (48%)*[6] | | 0.032 | 0.032 | 0.032 |
| | Methyl p-hydroxybenzoate*[14] | | 0.1 | 0.1 | 0.1 |
| | Phenoxyethanol*[15] | | 0.3 | 0.3 | 0.3 |
| D | Water | | 76.448 | 76.043 | 76.448 |
| | Total | | 100 | 100 | 100 |
| | Total amount of water | | 76.465 | 76.060 | 76.465 |
| | Average particle size (μm) | | 10 | 10 | 10 |
| | Viscosity (mPa · s) | | 1200 | 1200 | 1200 |
| | A/(A + C) | | 0.14 | 0.14 | 0.14 |
| | B/A | | 0.038 | 0.038 | 0.038 |
| | A/D | | 0.026 | 0.026 | 0.026 |
| | A/E | | 44 | 4.4 | 44 |
| | B/D | | 0.0010 | 0.0010 | 0.0010 |
| | A/F | | 0.222 | 0.222 | 0.222 |
| | B/F | | 0.008 | 0.008 | 0.008 |
| | Nonionic surfactant/total amount of oil agents | | 0.004 | 0.038 | 0.004 |
| | Three-layer structure nonwoven*[7] | | YES | YES | YES |
| | Basis weight (g/m$^2$) | | 58 | 58 | 58 |
| | Average fiber diameter (μm) | | 17 | 17 | 17 |
| | Thickness (μm) | | 450 | 450 | 450 |
| | Rate of impregnation (%) | | 500 | 500 | 500 |
| Evaluation | Sustention of moist feeling of skin after wiping | | 25 | 25 | 25 |
| | Sustention of soft and bouncy feeling of skin after wiping | | 25 | 25 | 25 |
| | Fresh feeling immediately after wiping | | 25 | 24 | 24 |
| | Moist feeling immediately after wiping | | 25 | 25 | 25 |
| | Feeling upon application after preservation | | 25 | 25 | 25 |
| | Thick feeling | | 25 | 25 | 25 |
| | Manageability (no dripping) | | 25 | 25 | 25 |
| | Smoothness in wiping | | 25 | 25 | 25 |
| | Cleansing power against oil-based mascara | | 25 | 23 | 25 |
| | Absence of stickiness | | 25 | 23 | 24 |

*[1]dioctyl ether: CETIOL OE (manufactured by BASF Japan Ltd.)
*[3]isododecane: MARUKASOL R (manufactured by Maruzen Petrochemical Co., Ltd.)
*[5]PEMULEN TR-2 (manufactured by Lubrizol Advanced Materials, Inc.)
*[10]polyoxypropylene (9) diglyceryl ether: SY-DP9 (manufactured by Sakamoto Yakuhin Kogyo Co., Ltd.)
*[12]1,3-butylene glycol: 1,3-Butylene Glycol-P (manufactured by KH Neochem Co., Ltd.)
*[13]polyethylene glycol (12) monolaurate: EMANON 1112 (manufactured by Kao Corp.)
*[6]liquid potassium hydroxide (48%): (manufactured by Asahi Glass Co., Ltd.)
*[14]methyl p-hydroxybenzoate: MEKKINSU M (manufactured by Ueno Fine Chemicals Industry, Ltd.)
*[15]phenoxyethanol: NEOLONE PH 100 (manufactured by the Down Chemical Company)
*[7]three-layer structure nonwoven: CT-58MS (manufactured by Daiwabo Co., Ltd.; cotton: 55%, pulp: 45%, density: 0.13 g/cm$^3$, basis weight: 58 g/m$^2$, thickness: 0.45 mm)

Examples 18 to 24 and Comparative Examples 15 to 20

Each skin cleansing sheet was produced using the nonwoven and the O/W emulsion shown in Table 5 and evaluated for the cleansing power, the stability, the thick feeling of the sheet, the softness of the sheet, the smoothness of the sheet, the fresh feeling, and the feeling from the amount of the solution contained in the sheet upon wiping. The results are also shown in Table 5.

The viscosity of the O/W emulsion was measured using a BM-type viscometer (manufactured by Tokimec, Inc., measurement conditions: rotor No. 2, 6 rpm, 1 min.). The respective rates of impregnation of the first layer and the second layers in the nonwoven were evaluated by the following method.

(Method for Evaluating Respective Rates of Impregnation (%) of First Layer and Second Layers in Nonwoven)

Each set involved the first layer and the second layers respectively disposed on the upper and lower surfaces of the first layer. Twenty sets were laminated and left standing at 50° C. for 1 month. Then, the respective rates of impregnation of the first layers (a sum of 2) and the second layers (a sum of 4) of the 10th and 11th sets counted from the top were measured, and an average value thereof was used as the rate of impregnation.

(Production Method)

Water as the component (M) was placed in a container at room temperature, and the component (J) was added thereto with stirring using Disper. As necessary, a base was added thereto, and the mixture was stirred. The components (H), (I), and (K) were further added thereto, and the mixture was stirred using a homomixer to obtain an O/W emulsion. The obtained O/W emulsion was applied to a nonwoven by dropwise addition or falling from a nozzle, or a nonwoven was impregnated with the O/W emulsion by spraying. Then, the nonwoven was left such that the O/W emulsion was fully spread in the sheet to produce a skin cleansing sheet.

(Evaluation Method)

(1) Cleansing Power:

0.005 g of KOSE Sports Beauty Fasio Power Stay Mascara (Curl Long) BK001 (trade name) was uniformly applied as oil-based mascara (waterproof mascara) in a circular pattern of 1.2 cm in diameter onto a polypropylene plate (manufactured by Engineering Test Service (ETS)) and left for 2 hours for drying. Each skin cleansing sheet was put on the oil-based mascara and lightly pressed for 10 seconds. Then, the oil-based mascara was wiped off at a given pressure (7.8 kPa). The number of wipes necessary for removing the mascara was measured and indicated according to the following criteria:

5: 5 or less.
4: 6 to 9.
3: 10 to 15.
2: 16 to 20.
1: 21 or more.

(2) Stability (Laminated Sheets):

Each nonwoven of 10 cm×10 cm was evenly impregnated with each O/W emulsion such that the predetermined rate of impregnation shown in the table was attained with respect to the dry mass of the nonwoven to prepare a skin cleansing sheet. Forty pieces of this skin cleansing sheet were laminated and left standing at 50° C. for 1 month. Then, when use of the uppermost sheet and the lowermost sheet in the laminated sheets was compared, five expert panelists wiped their foundation (Sofina Primavista Liquid Foundation Ocher 05; the same foundation was used in subsequent evaluations)-applied faces using the uppermost sheet and the lowermost sheet and evaluated difference in a feeling upon application therebetween according to five levels given below. The sum of the scores of the five panelists was used for determination.

5: Same.
4: Not so different.
3: Neutral.
2: Slightly different.
1: Different.

(3) Thick Feeling of Sheet:

Each nonwoven of 10 cm×10 cm was evenly impregnated with each O/W emulsion such that the predetermined rate of impregnation shown in the table was attained with respect to the dry mass of the nonwoven to prepare a skin cleansing sheet. Five expert panelists wiped their foundation-applied faces with each skin cleansing sheet and evaluated a thick feeling of the sheet upon wiping according to five levels given below. The sum of the scores of the five panelists was used for determination.

5: Thick feeling was perceived.
4: Thick feeling was slightly perceived.
3: Neutral.
2: Thick feeling was hardly perceived.
1: Thick feeling was absent.

(4) Softness of Sheet:

Each nonwoven of 10 cm×10 cm was evenly impregnated with each O/W emulsion such that the predetermined rate of impregnation shown in the table was attained with respect to the dry mass of the nonwoven to prepare a skin cleansing sheet. Five expert panelists wiped their foundation-applied faces with each skin cleansing sheet and evaluated the softness of the skin cleansing sheet upon wiping according to five levels given below. The sum of the scores of the five panelists was used for determination.

5: Soft.
4: Slightly soft.
3: Neutral.
2: Not so soft.
1: Not soft at all.

(5) Smoothness of Sheet:

Each nonwoven of 10 cm×10 cm was evenly impregnated with each O/W emulsion such that the predetermined rate of impregnation shown in the table was attained with respect to the dry mass of the nonwoven to prepare a skin cleansing sheet. Five expert panelists wiped their foundation-applied faces with each skin cleansing sheet and evaluated smooth wiping according to five levels given below. The sum of the scores of the five panelists was used for determination.

5: Smooth.
4: Slightly smooth.
3: Neutral.
2: Not so smooth.
1: Not smooth at all.

(6) Fresh Feeling:

Each nonwoven of 10 cm×10 cm was evenly impregnated with each O/W emulsion such that the predetermined rate of impregnation shown in the table was attained with respect to the dry mass of the nonwoven to prepare a skin cleansing sheet. Five expert panelists wiped their foundation-applied faces with each skin cleansing sheet and evaluated a fresh feeling upon wiping according to five levels given below. The sum of the scores of the five panelists was used for determination.

5: Fresh.
4: Slightly fresh.
3: Neutral.
2: Not so fresh.
1: Not fresh at all.

(7) Feeling from Amount of Solution Contained in Sheet Upon Wiping:

Each nonwoven of 10 cm×10 cm was evenly impregnated with each O/W emulsion such that the predetermined rate of impregnation shown in the table was attained with respect to the dry mass of the nonwoven to prepare a skin cleansing sheet. Five expert panelists wiped their foundation-applied faces with each skin cleansing sheet and evaluated the amount of the solution perceived by the skin upon wiping according to five levels given below. The sum of the scores of the five panelists was used for determination. A feeling that the amount of the solution was large allows a user to feel gentle upon wiping.

5: Felt that the amount of the solution was large.
4: Felt that the amount of the solution was slightly large.
3: Neutral.
2: Felt that the amount of the solution was slightly small.
1: Felt that the amount of the solution was small.

TABLE 5

| | | | | Example | | | | | | |
|---|---|---|---|---|---|---|---|---|---|---|
| | | | | 18 | 19 | 20 | 21 | 22 | 23 | 24 |
| Nonwoven | Combined-filament yarn single-layer structure (basis weight: (g/m²)) | Cotton | | — | — | — | — | — | — | — |
| | | Lyocell | | — | — | — | — | — | — | — |
| | | Pulp | | — | — | — | — | — | — | — |
| | Three-layer structure (basis weight: (g/m²)) | Total sum of second layers (g/m²) | Cotton | 38 | 26 | 32 | 38 | 27 | 32 | 32 |
| | | | PET | 0 | 0 | 0 | 0 | 11 | 0 | 0 |
| | | First layer (g/m²) | Pulp | 17 | 26 | 26 | 26 | 17 | 26 | 26 |
| | Average fiber diameter (μm) | | | 17 | 18 | 17 | 17 | 13 | 17 | 17 |
| | Total basis weight (g/m²) | | | 55 | 52 | 58 | 64 | 55 | 58 | 58 |
| | Total thickness (μm) | | | 450 | 430 | 450 | 470 | 420 | 450 | 450 |
| | Saturation water level (%) | | | 950 | 830 | 890 | 950 | 790 | 890 | 890 |
| | Ratio of (cotton) to (cotton) + (pulp) (%) | | | 69 | 50 | 55 | 59 | 61 | 55 | 55 |
| | Thickness of first layer (μm) | | | 110 | 170 | 170 | 170 | 110 | 170 | 170 |
| | Thickness of second layers (μm) | | | 170 | 130 | 140 | 150 | 155 | 140 | 140 |
| | Density of first layer (g/cm³) | | | 0.15 | 0.15 | 0.15 | 0.15 | 0.15 | 0.15 | 0.15 |
| | Density of second layers (g/cm³) | | | 0.11 | 0.10 | 0.11 | 0.13 | 0.12 | 0.11 | 0.11 |
| | Density (g/cm³) | | | — | — | — | — | — | — | — |
| | Ratio of density (first layer/second layers) | | | 1.38 | 1.53 | 1.34 | 1.21 | 1.26 | 1.34 | 1.34 |
| O/W EMULSION (mass %) | I | Isododecane*¹ (3 mPa · s) | | 12 | 12 | 12 | 12 | 12 | 12 | 12 |
| | H | Dioctyl ether*² | | 2 | 2 | 2 | 2 | 2 | 2 | 2 |
| | J | Hydroxyethylcellulose*³ | | 0.1 | 0.1 | 0.1 | 0.1 | 0.1 | 0.1 | 0.1 |
| | J | Acrylic acid/alkyl methacrylate copolymer*⁴ | | 0.075 | 0.075 | 0.075 | 0.075 | 0.075 | 0.075 | 0.075 |
| | | Potassium hydroxide solution (48%) | | 0.032 | 0.032 | 0.032 | 0.032 | 0.032 | 0.032 | 0.032 |
| | K | 1,3-Butylene glycol | | 5 | 5 | 5 | 5 | 5 | 5 | 5 |
| | K | Polyoxypropylene (9) diglyceryl ether*⁵ | | 4 | 4 | 4 | 4 | 4 | 4 | 4 |
| | L | Polyethylene glycol (12) monolaurate*⁶ (HLB:13) | | 0.045 | 0.045 | 0.045 | 0.045 | 0.045 | 0.045 | 0.045 |
| | M | Water | | 76.748 | 76.748 | 76.748 | 76.748 | 76/48 | 76.748 | 76.748 |
| | | Total | | 100 | 100 | 100 | 100 | 100 | 100 | 100 |
| | | Viscosity (mPa · s) | | 1200 | 1200 | 1200 | 1200 | 1200 | 1200 | 1200 |
| Rate of impregnation (%) | | | | 500 | 500 | 500 | 500 | 500 | 300 | 700 |
| Thickness of impregnated sheet (μm) | | | | 450 | 410 | 430 | 450 | 450 | 430 | 430 |
| Evaluation | Cleansing power | | | 5 | 5 | 5 | 5 | 5 | 4 | 5 |
| | Stability | | | 21 | 24 | 25 | 24 | 21 | 23 | 21 |
| | Thick feeling of sheet | | | 22 | 21 | 24 | 25 | 22 | 23 | 24 |
| | Softness of sheet | | | 21 | 23 | 25 | 21 | 21 | 20 | 25 |
| | Smoothness of sheet | | | 23 | 24 | 25 | 25 | 20 | 20 | 24 |
| | Fresh feeling | | | 24 | 24 | 25 | 24 | 22 | 22 | 22 |
| | Feeling from amount of solution contained in sheet upon wiping | | | 24 | 25 | 25 | 25 | 22 | 22 | 25 |
| Nonwoven | Rate of impregnation of first layer (%) | | | 240 | 250 | 250 | 250 | 240 | 95 | 300 |
| | Rate of impregnation of second layers (%) | | | 610 | 750 | 700 | 670 | 610 | 465 | 1020 |
| | Amount of solution per unit volume of second layers (g/m³) | | | $1.36 \times 10^6$ | $1.50 \times 10^6$ | $1.60 \times 10^6$ | $1.70 \times 10^6$ | $1.50 \times 10^6$ | $1.06 \times 10^6$ | $2.33 \times 10^6$ |
| | Ratio of thickness of first layer to thickness of one of second layers in nonwoven (thickness of first layer/thickness of one of second layers) | | | 0.65 | 1.31 | 1.21 | 1.13 | 0.71 | 1.21 | 1.21 |

| | | | | Comparative Example | | | | | |
|---|---|---|---|---|---|---|---|---|---|
| | | | | 15 | 16 | 17 | 18 | 19 | 20 |
| Nonwoven | Combined-filament yarn single-layer structure (basis weight: (g/m²)) | Cotton | | 41 | 41 | 41 | 32 | 0 | |
| | | Lyocell | | 18 | 18 | 18 | 0 | 0 | |
| | | Pulp | | 0 | 0 | 0 | 0 | 26 | |
| | Three-layer structure (basis weight: (g/m²)) | Total sum of second layers (g/m²) | Cotton | — | — | — | — | — | 53 |
| | | | PET | — | — | — | — | — | 0 |
| | | First layer (g/m²) | Pulp | — | — | — | — | — | 17 |

TABLE 5-continued

|  |  |  |  |  |  |  |  |  |
|---|---|---|---|---|---|---|---|---|
|  |  | Average fiber diameter (μm) |  | 14 | 14 | 14 | 15 | 20 |  |
|  |  | Total basis weight (g/m²) |  | 59 | 59 | 59 | 32 | 26 | 70 |
|  |  | Total thickness (μm) |  | 400 | 400 | 400 | 280 | 170 | 720 |
|  |  | Saturation water level (%) |  | 730 | 730 | 730 | 730 | 250 | >900 |
|  |  | Ratio of (cotton) to (cotton) + (pulp) (%) |  | 100 | 100 | 100 | 100 | 0 | 76 |
|  |  | Thickness of first layer (μm) |  | — | — | — | — | — | 100 |
|  |  | Thickness of second layers (μm) |  | — | — | — | — | — | 305 |
|  |  | Density of first layer (g/cm³) |  | — | — | — | — | — | 15 |
|  |  | Density of second layers (g/cm³) |  | — | — | — | — | — | 0.087 |
|  |  | Density (g/cm³) |  | 0.15 | 0.15 | 0.15 | 0.11 | 0.15 |  |
|  |  | Ratio of density (first layer/second layers) |  | — | — | — | — | — | 1.72 |
| O/W EMULSION (mass %) | I | Isododecane*¹ (3 mPa · s) |  | 12 | 12 | 12 | 12 | 12 | 12 |
|  | H | Dioctyl ether*² |  | 2 | 2 | 2 | 2 | 2 | 2 |
|  | J | Hydroxyethylcellulose*³ |  | 0.1 | 0.1 | 0.1 | 0.1 | 0.1 | 0.1 |
|  | J | Acrylic acid/alkyl methacrylate copolymer*⁴ |  | 0.075 | 0.075 | 1 | 0.075 | 0.075 | 0.075 |
|  |  | Potassium hydroxide solution (48%) |  | 0.032 | 0.032 | 0.4 | 0.032 | 0.032 | 0.032 |
|  | K | 1,3-Butylene glycol |  | 5 | 5 | 5 | 5 | 5 | 5 |
|  | K | Polyoxypropylene (9) diglyceryl ether*⁵ |  | 4 | 4 | 4 | 4 | 4 | 4 |
|  | L | Polyethylene glycol (12) monolaurate*⁶ (HLB:13) |  | 0.045 | 0.045 | 0.045 | 0.045 | 0.045 | 0.045 |
|  | M | Water |  | 76.748 | 76.748 | 75.455 | 76.748 | 76.748 | 76.748 |
|  |  | Total |  | 100 | 100 | 100 | 100 | 100 | 100 |
|  |  | Viscosity (mPa · s) |  | 1200 | 1200 | 16000 | 1200 | 1200 | 1200 |
| Rate of impregnation (%) |  |  |  | 500 | 700 | 700 | 500 | 500 | 500 |
| Thickness of impregnated sheet (μm) |  |  |  | 400 | 400 | 400 | 300 | 130 | 410 |
| Evaluation |  | Cleansing power |  | 3 | 5 | 3 | 3 | 3 | 5 |
|  |  | Stability |  | 18 | 12 | 19 | 16 | 14 | 17 |
|  |  | Thick feeling of sheet |  | 12 | 13 | 15 | 12 | 11 | 25 |
|  |  | Softness of sheet |  | 12 | 12 | 11 | 19 | 19 | 23 |
|  |  | Smoothness of sheet |  | 22 | 22 | 20 | 20 | 20 | 20 |
|  |  | Fresh feeling |  | 22 | 20 | 12 | 22 | 20 | 20 |
|  |  | Feeling born amount of solution contained in sheet upon wiping |  | 15 | 23 | 15 | 15 | 15 | 16 |
| Nonwoven |  | Rate of impregnation of first layer (%) |  | — | — | — | — | — | 300 |
|  |  | Rate of impregnation of second layers (%) |  | — | — | — | — | — | 560 |
|  |  | Amount of solution per unit volume of second layers (g/m³) |  | — | — | — | — | — | 9.73 × 10⁶ |
|  |  | Ratio of thickness of first layer to thickness of one of second layers in nonwoven (thickness of first layer/thickness of one of second layers) |  | — | — | — | — | — | 0.33 |

*¹isododecane: MARUKASOL R (manufactured by Maruzen Petrochemical Co., Ltd.)
*²dioctyl ether: CETIOL OE (manufactured by BASF Japan Ltd.)
*³hydroxyethylcellulose: HEC Daicel SE400 (manufactured by Daicel FineChem Ltd.)
*⁴acrylic acid/alkyl methacrylate copolymer: PEMULEN TR-2 (manufactured by Lubrizol Advanced Materials, Inc.)
*⁵polyoxypropylene (9) diglyceryl ether SY-DP9 (manufactured by Sakamoto Yakuhin Kogyo Co., Ltd.)
*⁶polyethylene glycol (12) monolaurate: EMANON 1112 (manufactured by Kao Corp.)

Examples 25 to 28 and Comparative Examples 21 to 22

In the same way as in Examples 18 to 24, each skin cleansing sheet shown in Table 6 was produced. The skin cleansing sheet was evaluated for the cleansing power and the feeling from the amount of the solution contained in the sheet upon wiping and further evaluated for the feeling upon application after preservation and the feeling upon application immediately after impregnation. The results are also shown in Table 6.

(Evaluation Method)

(1) Feeling Upon Application after Preservation:

Forty sets of each skin cleansing sheet were laminated and preserved at 50° C. for 2 weeks. Then, five expert panelists compared a feeling upon application between the set positioned uppermost and the set positioned lowermost by wiping their foundation-applied faces and evaluated difference in the feeling upon application according to five levels given below. The sum of the scores of the five panelists was used for determination.

5: Same.
4: Not so different.
3: Neutral.
2: Slightly different.
1: Different.

(2) Feeling Upon Application Immediately after Impregnation:

Each nonwoven of 10 cm×10 cm was evenly impregnated with each O/W emulsion such that the predetermined rate of impregnation shown in the table was attained with respect to the dry mass of the nonwoven to prepare a skin cleansing sheet. Five expert panelists wiped their foundation-applied faces with each skin cleansing sheet and evaluated sliminess upon wiping according to five levels given below. The sum of the scores of the five panelists was used for determination.

5: Smooth without sliminess.
4: Slightly less slimy and smooth.
3: Neutral.
2: Slightly slimy and not so smooth.
1: Slimy and not smooth.

the mass ratio of component (B) to component (A), (B)/(A) is from 0.0001 to 0.1, and the mass ratio between component (A) and component (C), (A)/((A)+(C)) is from 0,05 to 0.9.

TABLE 6

|  |  |  |  | Example |  |  |  | Comparative Example |  |
|---|---|---|---|---|---|---|---|---|---|
|  |  |  |  | 25 | 26 | 27 | 28 | 21 | 22 |
| Nonwoven | Three-layer structure | Second layers (g/m²) | Cotton | 32 | 32 | 32 | 32 | 32 | 32 |
|  |  | First layer (g/m²) | Pulp | 26 | 26 | 26 | 26 | 26 | 26 |
|  |  | Total basis weight (g/m²) |  | 58 | 58 | 58 | 58 | 58 | 58 |
|  |  | Average fiber diameter (μm) |  | 17 | 17 | 17 | 17 | 17 | 17 |
|  |  | Thickness (μm) |  | 450 | 450 | 450 | 450 | 450 | 450 |
|  |  | Saturation water level (%) |  | 890 | 890 | 890 | 890 | 890 | 890 |
|  |  | Ratio of (cotton) to (cotton) + (pulp) (%) |  | 55 | 55 | 55 | 55 | 55 | 55 |
|  |  | Thickness of first layer (μm) |  | 170 | 170 | 170 | 170 | 170 | 170 |
|  |  | Thickness of second layers (μm) |  | 140 | 140 | 140 | 140 | 140 | 140 |
|  |  | Density of first layer (g/cm³) |  | 0.15 | 0.15 | 0.15 | 0.15 | 0.15 | 0.15 |
|  |  | Density of second layers (g/cm³) |  | 0.11 | 0.11 | 0.11 | 0.11 | 0.11 | 0.11 |
|  |  | Ratio of density (first layer/second layers) |  | 1.34 | 1.34 | 1.34 | 1.34 | 1.34 | 1.34 |
| O/W EMULSION (mass %) | I | Isododecane*[1] |  | 12 | 12 | 12 | 14 | 0 | 100 |
|  | H | Dioctyl ether*[2] |  | 2 | 2 | 2 | 0 | 0 | 0 |
|  | J | Hydroxyethylcellulose*[3] |  | 0.1 | 0.1 | 0.1 | 0 | 0 | 0 |
|  | J | Acrylic acid/alkyl methacrylate copolymer*[4] |  | 0.075 | 0.05 | 0.15 | 0.05 | 0 | 0 |
|  | K | 1,3-Butylene glycol |  | 5 | 5 | 5 | 5 | 0 | 0 |
|  | K | Polyoxypropylene (9) diglyceryl ether*[5] |  | 4 | 4 | 4 | 4 | 0 | 0 |
|  | L | Polyethylene glycol (12) monolaurate*[6] |  | 0.045 | 0.045 | 0.045 | 0.045 | 0 | 0 |
|  |  | Potassium hydroxide solution (48%) |  | 0.032 | 0.02 | 0.064 | 0.04 | 0 | 0 |
|  | M | Water |  | 76.748 | 76.785 | 76.641 | 76.865 | 100 | 0 |
|  |  | Total |  | 100 | 100 | 100 | 100 | 100 | 100 |
|  |  | Viscosity (mPa · s) |  | 1200 | 400 | 2100 | 800 | 10 or less | 10 or less |
| Rate of impregnation (%) |  |  |  | 500 | 500 | 500 | 500 | 500 | 500 |
| Evaluation |  |  | Cleansing power | 5 | 5 | 4 | 4 | 1 | 5 |
|  |  |  | Feeling upon application after preservation | 25 | 20 | 25 | 21 | 11 | 11 |
|  |  |  | Feeling upon application immediately after impregnation | 25 | 25 | 21 | 21 | 15 | 11 |
|  |  |  | Feeling from amount of solution contained in sheet upon wiping | 25 | 25 | 23 | 25 | 22 | 13 |
| Nonwoven |  | Rate of impregnation of first layer (%) |  | 250 | 250 | 255 | 255 | 280 | 280 |
|  |  | Rate of impregnation of second layers (%) |  | 700 | 700 | 705 | 705 | 680 | 680 |
|  |  | Amount of solution per unit volume of second layers (g/m³) |  | 1.60 × 10⁶ | 1.60 × 10⁶ | 1.61 × 10⁶ | 1.61 × 10⁶ | 1.55 × 10⁶ | 1.55 × 10⁶ |
|  |  | Ratio of thickness of first layer to thickness of one of second layers in nonwoven (thickness of first layer/thickness of one of second layers) |  | 1.21 | 1.21 | 1.21 | 1.21 | 1.21 | 121 |

*[1]isododecane: MARUKASOL R (manufactured by Maruzen Petrochemical Co., Ltd.)
*[2]dioctyl ether: CETIOL OE (manufactured by BASF Japan Ltd.)
*[3]hydroxyethylcellulose: HEC Daicel SE400 (manufactured by Daicel FineChem Ltd.)
*[4]acrylic acid/alkyl methacrylate copolymer: PEMULEN TR-2 (manufactured by Lubrizol Advanced Materials, Inc.)
*[5]polyoxypropylene (9) diglyceryl ether: SY-DP9 (manufactured by Sakamoto Yakuhin Kogyo Co., Ltd.)
*[6]polyethylene glycol (12) monolaurate: EMANON 1112 (manufactured by Kao Corp.)

The invention claimed is:

1. A skin cleansing composition comprising components (A), (B), (C), (D), and (E):
    (A) 0.1 to 25 mass % of an ether oil which is in a liquid state at 25° C.,
    (B) 0.003 to 1 mass % of a water-soluble polymer comprising acrylic acid or methacrylic acid as a constitutional unit,
    (C) 1 to 30 mass % of a hydrocarbon oil having a viscosity of 15 mPa·s or lower at 30° C.,
    (D) 65 to 90 mass % of water, and
    (E) 0.49 mass % or less of a nonionic surfactant having an HLB of larger than 9, wherein 2. The skin cleansing composition according to claim 1, wherein the mass ratio of component (A) to component (D), (A)/(D) is 0.45 or less.

3. The skin cleansing composition according to claim 1, wherein component (A) is a dialkyl ether having two alkyl groups each having 16 or less of carbon atom.

4. The skin cleansing composition according to claim 1, wherein component (A) is a dialkyl ether having two alkyl groups each having 8 or less of carbon atom.

5. The skin cleansing composition according to claim 1, wherein component (B) is an acrylic acid/alkyl methacrylate copolymer.

6. The skin cleansing composition according to claim 1, wherein component (B) is a copolymer of acrylic acid and alkyl methacrylate having 10 to 30 of carbon atom.

7. The skin cleansing composition according to claim 1, wherein the mass ratio of component (A) to component (E), (A)/(E), is 0.1 to 200,000.

8. The skin cleansing composition according to claim 1, further comprising (F) a water-soluble solvent.

9. The skin cleansing composition according to claim 1, wherein the skin cleansing composition is in the form of a sheet impregnated therewith.

10. A skin cleansing sheet comprising a sheet impregnated with the skin cleansing composition according to claim 1.

11. The skin cleansing composition according to claim 1, wherein component (A) is one or two selected from the group consisting of cetyl-1,3-dimethyl butyl ether and dioctyl ether.

12. The skin cleansing composition according to claim 1, wherein the content of component (A) in the total composition is from 1 to 6 mass %.

13. The skin cleansing composition according to claim 1, wherein the content of component (B) in the total composition is from 0.05 to 0.1 mass %.

14. The skin cleansing composition according to claim 1, wherein the content of component (C) in the total composition is from 8 to 15 mass %.

15. A method of cleansing facial skin having a makeup cosmetic thereon, comprising applying a skin cleansing composition according to claim 1 to clean the facial skin having the makeup cosmetic thereon by removing at least a portion of the makeup cosmetic.

16. A method of cleaning facial skin having a makeup cosmetic thereon, the method comprising contacting the facial skin having the makeup cosmetic present thereon with a sheet having a skin cleansing composition according to claim 1 comprised therein to clean the facial skin by removing at least a portion of the makeup cosmetic.

17. The skin cleaning composition of claim 1,
wherein the ether oil component (A) is at least one selected from the group consisting of dioctyl ether, cetyl-1,3-dimethyl butyl ether, dihexyl ether, and dilauryl ether, and
wherein the hydrocarbon oil component (C) is at least one selected from the group consisting of isododecane, isohexadecane, and hydrogenated polyisobutene.

18. The skin cleansing composition of claim 1, wherein a content of oil agents other than the ether oil component (A) and the hydrocarbon oil component (C), if present, is 20 mass % or less.

* * * * *